US008784513B2

(12) United States Patent
Iversen et al.

(10) Patent No.: US 8,784,513 B2
(45) Date of Patent: Jul. 22, 2014

(54) METHOD AND APPARATUS FOR PRODUCTION OF BIO-ETHANOL AND OTHER FERMENTATION PRODUCTS

(75) Inventors: Steen Brummerstedt Iversen, Vedbæk (DK); Tommy Larsen, Slagelse (DK); Corinne Mallol, Bjuv (SE)

(73) Assignee: Altaca Insaat ve dis Ticaret A.S., Istanbul (TR)

( * ) Notice: Subject to any disclaimer, the term of this patent is extended or adjusted under 35 U.S.C. 154(b) by 1113 days.

(21) Appl. No.: 11/777,558

(22) Filed: Mar. 14, 2008

(65) Prior Publication Data
US 2008/0229653 A1 Sep. 25, 2008

(30) Foreign Application Priority Data

Jul. 14, 2006 (DK) .................................. 2006 00979

(51) Int. Cl.
C10L 1/18 (2006.01)

(52) U.S. Cl.
USPC ........................................ 44/307; 422/184.1

(58) Field of Classification Search
USPC ............................................. 127/36; 44/605
See application file for complete search history.

(56) References Cited

U.S. PATENT DOCUMENTS

| 4,334,026 | A | 6/1982 | Chynoweth et al. |
| 5,628,830 | A | * | 5/1997 | Brink ............................ 127/36 |
| 2006/0260186 | A1 | * | 11/2006 | Iversen et al. ............ 44/605 |
| 2009/0064566 | A1 | 3/2009 | Brummerstedt Iversen et al. |
| 2010/0015677 | A1 | 1/2010 | Iversen et al. |

FOREIGN PATENT DOCUMENTS

| CA | 2606762 A1 | 11/2011 |
| CN | 1138876 A | 12/1996 |
| EP | 1 184 443 A1 | 6/2002 |
| WO | 96/08575 | 3/1996 |
| WO | WO 00/00285 | 1/2000 |
| WO | 2006/117002 A2 | 11/2006 |
| WO | WO 2006/117002 A2 | 11/2006 |
| WO | WO 2007/059783 | 5/2007 |

OTHER PUBLICATIONS

Iversen et al., A disruptive technology for biomass conversion, 2005, p. 1, XP002428253.
Larsen, CHP plant based on catalyc liquid conversion process Catliq, May 2005, pp. 1-16, XP002428254.
Yingrui, W. "Study of the Application of Supercritical Water Oxidation to Molasses Alcohol Wastewater" Apr. 21, 2003, A dissertation submitted to Guangxi Normal University for the degree of Master. By postgraduate Wu Yingrui. (Abstract in English).
Jacob Becker-Christensen et al., "Synthesis of Nanoparticulate $Zr_{o2}$ Powders in Supercritical Media", iNano, 1 page, Denmark, (2002).
Carlo N. Hamelinck et al., "Production of FT Transportation Fuels From Biomass ; Technical Options, Process Analysis and Optimisation, and Development Potential", Elsevier, Energy 29 (2004) pp. 1743-1771.

(Continued)

Primary Examiner — Prem C Singh
Assistant Examiner — Chantel Graham
(74) Attorney, Agent, or Firm — Knobbe, Martens, Olson & Bear LLP

(57) ABSTRACT

The present invention relates to a method and apparatus for converting organic material into a burnable substance, typically a hydrocarbon fuel, such as ethanol.

71 Claims, 9 Drawing Sheets

(56) References Cited

OTHER PUBLICATIONS

S.B. Iversen et al., "CATLIQ™—A Disruptive Technology for Biomass Conversion", SCF-Technologies.com, 16 pages, Karlsruhe, Germany, (1981).

Kari Pirkanniemi et al., "Heterogeneous Water Phase Catalysis as an Environmental Application: A Review", Elsevier Ltd., Pergamon, Chemosphere 48 (2002) pp. 1047-1060.

J.H. Reith et al., "Co-Production of Bio-Ethanol, Electricity and Heat From Biomass Residues", 21 pages, (2001).

Jens R. Rostrup-Nielsen, "Making Fuels From Biomass", Science, vol. 308, Jun. 3, 2005, www.sciencemag.org, 1 page. (1421).

David S. Wilcove, "Rediscovery of the Ivory-Billed Woodpecker", Science, vol. 308, Jun. 3, 2005, www.sciencemag.org. 1 page (1422).

Reith et al., Co-Production of Bio-Ethanol, Electricity and Heat From Bio Mass Wastes: potential and R&D Issues. The First European Conference on Agriculture and Renewable Energy. May 6-8, 2001, RAI, Amsterdam, The Netherlands: 1-12.

Liscinsky et al., Biomass Gasification and Power Generation Using Advanced Gas Turbine Systems. Final Report United Technologies Research Center. Nov. 2001 to Sep. 2002.

European Standard Search Report dated Apr. 19, 2007 for PA 2006 00979.

International Search Report Dated Jul. 22, 2008 for PCT/DK2007/050098.

International Preliminary Report on Patentability Dated Dec. 8, 2008 for PCT/DK2007/050098.

Goudriann, F., Transportation Fuels From Biomass Via the HTU Process, 4$^{th}$ European Motor BioFuels Forum Conference Proceedings, Nov. 24-26, 2003, pp. 85-86, Biofuel b.v.

Mosier et al., Features of Promising Technologies for Pretreatment of Lignocellulosic Biomass, Bioresource Technology, 2005, pp. 673-686, 96, Elsevier.

\* cited by examiner

METHOD AND APPARATUS FOR PRODUCTION OF BIO-ETHANOL AND OTHER FERMENTATION PRODUCTS

The present invention relates to a method and apparatus for converting organic material into a burnable substance, typically a hydrocarbon fuel, such as ethanol.

BACKGROUND

The world's energy demand is increasing, and the fossil fuel sources are depleted, leading to increasing competition for the available energy sources, and thereby hampering economic growth by high energy prices. To overcome this situation, renewable energy sources must be brought into exploitation. With the present-day technology, the only renewable energy source which has sufficient capacity to cover significant parts of the energy demand is biomass conversion. Biomass is efficiently converted into heating and electricity by existing technologies, but transportation fuels, which accounts for one third of the total energy consumption, must be available as high energy density fluids, preferably compatible with fossil fuels like diesel oil and gasoline. Therefore technologies for transforming and intensifying the energy content of biomass are required.

Methods for producing bio-ethanol are known. It typically involves a number of unit operations such as feedstock preparation, fermentation and by-product purification. Each of these unit operations may comprise several unit operations. Such prior art method have a number of draw backs. Firstly, bio-ethanol is mainly produced from starch and sugar rich biomass such as corn and wheat grain. Already in the feedstock harvesting step ½ to ⅔ of the plant material is often rejected, and mainly the seeds are used in the fermentation. Various methods are being developed to increase the amount of plant material which can be converted in the conversion step. Such methods include enzymatic hydrolysis of the starch to produce glucose which can be converted in the fermentation. Typically the entire feed stock is processed i.e. the feed pulp also includes the cellulostic parts and other materials, which are not converted in the fermentation. Hence, prior art methods include up-grading the residual material from the fermentation to a dry material after separation from the ethanol produced. This upgraded material may be used as cattle feed. The market for the upgraded by-product is not expected to match the production, if a large number of bio-ethanol plants are put into operation. It is therefore desirable to find an alternative use of the by-product. Secondly many of the unit operations involved in prior art method have a relative high energy consumption thereby increasing the production cost of the bio-ethanol. Thirdly a large amount of the plant installation cost is related to up-grading of the residual material e.g. decanting and drying, and especially the drying is very energy consuming. Furthermore, existing methods for producing bio-ethanol is limited to specific feed stock. It is highly desirable to enable conversion of other materials such as waste materials eventually in to other types of products, such as oils.

SUMMARY OF THE INVENTION

An objective of the present invention is to provide an improved method and an improved apparatus for converting organic material, such as waste, sludge, biomass etc., into hydrocarbon products, such as hydrocarbon fuel.

Another objective of the present invention is to provide a method and an apparatus for more effective production of fermentation products such as bio-ethanol. Efficiency in this context should be interpreted in broad terms such as cost efficiency, energy efficiency, yield, new uses of residual products etc.

It is still another objective to provide a method and apparatus expanding the amount and types of organic materials that can be converted by the process.

A further objective of the present invention is to provide an improved recyclable product from the conversion of organic material, which improved product is reusable as some kind of energy. These objectives and several others objectives, which will become evident below, are obtained by a first aspect of the present invention by providing a method for converting organic material into hydrocarbon fuel, such as ethanol, the method comprising
- a fermentation process fermenting the organic material thereby providing a fermentation broth,
- a separation process separating the fermented material into a hydrocarbon fuel and a residual product,
- a conversion process at least partly converting the residual product into energy,
- energy distribution process distributing at least some of the energy provided by the conversion process to the fermentation process.

The separation process may also be termed a purification process.

The conversion into energy typically, but not exclusively, includes a conversion into thermal energy such as heat.

The term "hydrocarbon fuel" is to be understood in broad sense, typically as a burnable substance containing hydrocarbons, such as hydrocarbon based fuel, which may or may not comprise other elements than carbon and hydrogen, e.g. some of said hydrocarbons may comprise oxygen and other elements e.g. in the form of groups of alcohols, aldehydes, ketones, carboxylic acids, esters, ethers and reaction products thereof. In particular hydrocarbons according to the present invention include oils, such as bio-crude, bio-oil, bio-diesel, and alcohols such as methanol, ethanol, propanol, iso-propanol, In a preferred embodiment according to the present invention involves the hydrocarbon fuel comprises ethanol. Further said ethanol production may have an overall positive energy economy, and the yield of ethanol may be substantially unchanged by said conversion process.

Ethanol production according to the present invention often comprise further comprising one or more pre-treatment process producing a mash from the organic material for the fermentation process. Such pre-treatment process may comprise a milling of the organic material such a milling by a wet and/or dry milling. In this milling process the feedstock material is divided into smaller parts. Water may be added either before the milling step (wet milling) or after the milling (dry milling) to produce a feed pulp. Normally the entire feedstock is processed, i.e. the feed pulp includes also the cellulostic and protein part of the seeds. The pre-treatment may further include a liquefaction step. Enzymes may be added to the pulp in the liquefaction step to break down the plant material structure by hydrolysis and liberate starch from the seeds. The starch is further hydrolysed to smaller sugars—dextrins. Still further the pre-treatment may include a subsequent saccharification step. In this step dextrins may be broken down to low molecular weight sugars suitable for fermentation. The saccharification may be performed by enzymatic hydrolysis using a mixture of enzymes.

A preferred embodiment according to the present invention is where at least 50% of the energy required for said pre-treatment process being supplied by said energy distribution process, such as at least 70% of the energy required for said pre-treatment process being supplied by said energy distribution process, and preferably at least 80% of the energy required for said pre-treatment process being supplied by said energy distribution process, such as at least 90% of the energy required for said pre-treatment process being supplied by said energy distribution process, and even more preferably at least 95% of the energy required for said pre-treatment process being supplied by said energy distribution process, such as substantially all of the heat required for said pre-treatment process being supplied by said energy distribution process.

In most embodiments according to the present invention the fermentation process takes place in a fluid, preferably being water. The fermentation process often comprises converting sugar(s) by use and/or addition of micro organism(s), such as yeast, and/or bacterias such as thermolabile bacterias directly and/or indirectly into the fermentation broth comprising hydrocarbon fuel(s). Often the fermentation process takes place at a temperature between 24-36° C. for 24-96 hours in an environment with a pH around 4-5.

The separation process preferably comprises distilling the fermentation broth whereby at least a part of the hydrocarbon fuel is separated from the fermentation broth. Additionally, substantial all of the hydrocarbon fuel and residual products present in the fermentation broth is separated subsequent to the fermentation process, and wherein substantially all of the hydrocarbon fuel present in the fermentation broth is distilled off. Furthermore, the hydrocarbon fuel may preferably be ethanol, and the ethanol after said distillation process is preferably substantially in the form azeotropic mixture of ethanol and water.

The method according to the present invention may preferably further comprise a hydrocarbon fuel separation process, wherein water is removed from the hydrocarbon fuel. Additionally, said further hydrocarbon separation process may include a membrane process such as a pervaporation. Alternatively or in combination thereto, water may be removed from said hydrocarbon fuel by a molecular sieving process. The molecular sieving process may preferably include a zeolite.

The separation process for separating said hydrocarbon fuel from the fermentation broth is an energy demanding process. Hence, in a preferred embodiment according to the present invention at least 50% of the energy required for said separation process is being supplied by said energy distribution process, such as at least 70% of the energy required for said separation process being supplied by said energy distribution process, and preferably at least 80% of the energy required for said separation process being supplied by said energy distribution process, such as at least 90% of the energy required for said separation process being supplied by said energy distribution process, and even more preferably at least 95% of the energy required for said separation process being supplied by said energy distribution process, such as substantially all of the heat required for said separation process being supplied by said energy distribution process.

The remaining fermentation broth subsequent to said separation process for separation and separation of said hydrocarbon fuel, hereinafter called the fermentation rest or residual product typically may include unconverted starch, other organics from the feed stock like cellulostic material, proteins and other feed stock cell material as well as dead yeast cells, microorganisms, enzymes etc. Known techniques typically process this fermentation rest or residual product to animal fodder which can be used to feed e.g cattles. Such processing typically include numerous steps including decanting and/or drying operatins so as to obtain a substantially dry material called "Dried distilled Grains with solubles (DDGS), which is sold as animal fodder. The processing steps involved have a high energy consumption and the value of the animal fodder product is relatively low. Hence, such upgrading of the residual product adds to the processing costs and makes it less competitive. Further the market for such upgraded by-product is not expected to match the production of the hydrocarbon fuel, if a larger number of such plants are put into operation.

Hence, it is desirable to find alternative uses of this fermentation rest or residual product. The present invention provides a method for converting such residual product by to some kind of energy and at least partly distributing this energy back to the pre-treatment process and/or the fermentation process and/or the separation process.

In preferred embodiments of the method according to the present invention at least 50% of the energy required for said pre-treatment process, fermentation process, and separation process is being supplied by said energy distribution process, such as at least 70% of the energy required for said pre-treatment process, fermentation process, and separation process being supplied by said energy distribution process, and preferably at least 80% of the energy required for said pre-treatment process, fermentation process, and separation process being supplied by said energy distribution process, such as at least 90% of the energy required for said pre-treatment process, fermentation process, and separation process being supplied by said energy distribution process, and even more preferably at least 95% of the energy required for said pre-treatment process, fermentation process, and separation process being supplied by said energy distribution process, such as substantially all of the heat required for said pre-treatment process, fermentation process, and separation process being supplied by said energy distribution process.

One embodiment said conversion process for converting said residual product comprises a combustion process and/or a gasification process and/or a pyrolysis process. Said combustion and/or gasification and/or a pyrolysis process for converting said residual product to energy may be a thermal process. In such embodiments the conversion process may further comprise a drying process using some kind of waste heat source. Said waste heat source may be a hot gas and/or low pressure steam and/or a hot water, e.g. an excess energy stream from e.g. power and/heat production by prior art processes.

However, the fermentation rest or residual product typically contains more than 80% water by weight, such as more than 90% by weight and may contain as much as 95% by weight, and the energy consumption for evaporating such large amounts of water, makes it difficult to obtain a positive energy.

Hence, in an aspect of the present invention said conversion process occurs in a media such as a fluid such as water and the conversion process occurs without the need to supply the heat of evaporation for the water contained in said fermentation rest or residual product. In one embodiment this is provided by conversion process comprising a bio-gasification, wherein said fermentation rest or residual product is converted into a bio-gas, which may or may not be combusted or burned in a subsequent step so as to provide heat and/or steam and/or a hot water stream for said energy distribution process.

The feedstock to said conversion process according to the present invention may comprise other feedstock materials than said fermentation rest or residual product from the fermentation and/or separation process. Prior art methods typically only use between ⅓ and ½ of the plant material harvested is used as feedstock to the pre-treatment and fermentation processes, and residues such as leaves and straw is typically not used in the fermentation process for production of hydrocarbon fuels. Such residues from the harvesting may be mixed with said fermentation rest or said residual product prior to said fermentation process, and thereby increase or improve the overall efficiency.

In some embodiments other materials such as waste materials may be mixed with said fermentation rest and/or residual product prior to said conversion process.

An attractive embodiment of the present invention is to conduct said conversion in a high pressure fluid such as in a fluid at a pressure of at least 50 bar, such as at pressure of least 100 bar and preferably at a pressure of at least 150 bar such at a pressure of at least 200 bar such as at a pressure of at least 250 bar. Said fluid may be selected among water and/or alcohols and mixtures thereof. Often said conversion in said high pressure fluid involves a hydrothermal and/or solvothermal conversion process i.e. said conversion at least partly include a thermal degradation of said substances contained in said fluid.

The conversion process may be a combustion process in such high pressure fluid such as a supercritical water oxidation or a partial oxidation process, wherein an oxidant such as oxygen is added to the fluid or fluid mixture so as to at least partially oxidize or convert said organic materials by the action of said oxidant using said fluid as reaction media.

In another embodiment said conversion process in said high pressure fluid comprises conversion by a "wet gasification" and/or "liquefaction" process within said high pressure fluid. Furthermore said gas or liquid may be combusted or converted into a another energy source such as hot gas and/or steam and/or hot water before being distributed to said energy distribution process.

An attractive embodiment of the present invention is provided by the use of homogeneous and/or heterogeneous catalysts present within said high pressure fluid, thereby enhancing the reaction rate and promoting conversion into a desired product. In many embodiments according to the present invention said homogeneous and/or heterogeneous catalysts comprises at least one compound from the group 1 of the periodic table of elements. In a even more preferable embodiment a heterogeneous catalyst is also present and/or contacted with said high pressure fluid. Said heterogeneous catalysts may comprise at least one of the elements Zr, Ti, Al, Si, Fe, Ni, Co, Cr, W, Mo, V, Sn, Zn, Ru, and preferably said heterogeneous catalyst are present in the form of an oxide and/or oxyhydroxide.

The temperature of said conversion process may according to the present invention may be up to 700 C, such as up to 600 C and preferably up to 500 C such as up 400 C, and even more preferably up to 350 C such as up to 250 C.

The at least one homogeneous and/or heterogeneous catalysts may preferably comprise at least one compound of at least one element from group I of the periodic table and/or at least one compound of at least one element from group IV of the periodic table.

Preferably, at least one homogeneous and/or heterogeneous catalyst may be contained in the ash fraction of said substances being fed to said conversion step.

Another aspect of the present invention provides a method for converting a residual product into hydrocarbon fuels. The residual product is preferably provided by a method according to first aspect of the present invention and the method preferably comprises the steps of:

pressurising said residual product in a fluid to a pressure above 225 bar, and heating said residual product in said fluid to a temperature above 200 C in the presence of a homogeneous catalyst comprising a compound of at least one element of group I of the periodic table of elements, wherein the method further comprises the steps of:

contacting said residual product in said fluid with a heterogeneous catalyst comprising a compound of at least one element of group IVB of the periodic table and/or alpha-alumina.

Preferably, the method may further comprise a step of assuring that said fluid has initially a pH value of above 7, preferably by adjusting said fluid to have a pH value above 7.

An improved method for converting a residual product into recyclable products is hereby obtained. By contacting the residual product with a heterogeneous catalyst comprising a compound of at least one element of group IVB of the periodic table and/or alpha-alumina, the catalyst may be reused and a continuously converting of residual product is possible. Thereby the amount of catalyst spent for converting one amount of residual product is decreased whereby the cost for converting the material is considerable decreased. Additionally, the process time has been decreased considerably due to the fact that dividing the catalyst process into two separate processes increases the velocity of conversion.

Furthermore, by adjusting the fluid to above 7 the corrosion of the materials used for the involved components in the apparatus is considerably decreased. The corrosion of these materials has decreased to such an amount that cheap standard materials may be used for the construction of the apparatus.

According to another aspect of the present invention the method may comprise the step of maintaining the pH value of said fluid containing said residual product in the range 7-14, such as 7-12 and preferably in the range 7-10 such as in the range 7-9.5, and preferably in the range of 8-10. It is hereby obtained that when converting the residual product into hydrocarbon fuel the corrosion of the materials used for the involved components of the apparatus is substantial decreased to at least an insignificant amount of corrosion.

Furthermore, according to an aspect of the present invention the method may comprise the step of pre-treating the residual product at a pressure of 4-15 bar at the temperature of 100-170 C for a period of 0.5-2 hours. In another aspect of the present invention the method may comprise the step of pre-treating the residual product by an enzymatic treatment at a temperature of 20-100 C. By such a pre-treatment the residual product, the residual product is pre-converted whereby the subsequent conversion may be performed more quickly than without the pre-treatment.

Subsequently, the pre-treating step may according to another aspect of the invention comprise a step of size reducing of the material such as a cutting, grinding, milling, or sieving step or a combination thereof. By such a size reduction the conversion process of the residual product is performed even more quickly than without the size reduction.

Additionally, the pre-treating step may comprise the step of adding additives to the fluid according to the present invention, whereby the conversion process is improved even further in regards to speed of the conversion time and in regards to the resulting product from the conversion of the residual product into hydrocarbon fuels. The product resulting from the conversion of the residual product may by adding these additives be regulated, so that the resulting product may have variable composition of oil, methanol, water, water soluble organics, water soluble salts, etc. It is then possible to adjust the recyclable product in regards to the wishes of the subsequent use of the products.

In one aspect of the present invention the step of pre-treating may comprise the step of adjusting the pH of said fluid comprising said residual product to above 7. It hereby obtained to adjustment of the pH value in the fluid comprising the residual product at an early stage of the conversion process, whereby the process time for the conversion is reduced.

By the step of pre-treating the fluid comprising the residual product it is possible to increase the amount of solid-state material in the fluid, which again leads to a higher rate of conversion and thereby a higher production capacity. This results in a more efficient and cost saving converting of organic material.

In another aspect of the present invention the method may further comprise a step of separating particles from the fluid comprising the organic material. By separating particles before contacting the fluid comprising the residual product with the heterogeneous catalyst the product resulting from the conversion process, such as oil, is then substantially free of being bound to these particles and therefore much more reusable straight after this conversion process. A second process, such as an refinery is thereby dispensable.

In yet another aspect of the present invention the method may further comprise a second step of heating the fluid. The temperature of fluid comprising the residual product is hereby adjustable just before contacting the heterogeneous catalyst, whereby the process is optimised, which leads to a reduced process time. Furthermore, by separating the particles away from the fluid at such an early stage a substantially amount of energy for transporting the separated particles is saved, which again decreases the amount of energy spend in the conversion process as a total.

Additionally, the method may according to the invention comprise a second separating of particles, which step is merely for safety reason in regards to the first step of separating particles. This step reduces for the same reasons as the first step of separating particles the total amount of energy spend for the conversion process.

Furthermore, the method may according to the invention comprise a step of cooling the fluid. By cooling the fluid the resulting product from converting of the residual product may be optimized in relations to the composition of product.

Advantageously, the step of cooling may according to the present invention be performed by heat exchanging with the first step of heating and/or a step of pre-heating the fluid in the pre-treating step. It is hereby obtained to reuse the heat from the fluid, which needs to cool down before the second part of conversion into the recyclable products, in the fluid in the first part of conversion process before contacting the fluid with the heterogeneous catalyst. The total amount of energy for the converting of residual product is thereby kept to a minimum.

Said method may according to one aspect the present invention further comprise a step of separating gas from the fluid, such as fuel gas. By separating this gas one kind of recyclable product is obtained, which was an objective of the invention.

The method may according to one aspect the present invention further comprise the step that the fuel gas is used for heating the fluid in the second heating step. By using the separated gas it is reused in converting the residual product and therefore reusable.

Furthermore, the method may according to the invention further comprise a step of separating the fluid into water and water soluble organics from oil and water soluble salts in a first separating unit such as a membrane-filter. By this separating a recyclable products is obtained and a further converting into recyclable products is possible.

In an aspect of the present invention the water and water soluble organics are transformed into electricity in a direct methanol fuel cell. This is one way of using one of the recyclable products of the present invention. It may also be regarded as a subsequent step of converting the recycle products into a usable product in form of electricity.

The method may also according to another aspect of the present invention comprise a second step of separating, such as filtering water soluble organics from the water, such as an separation of methanol in a second separating unit such as a membrane-filter. By this conversion step one recycle product is obtained.

Subsequently, said one or more separation units may be selected from the group of phase separators, centrifuges, membrane processes comprising ultra-filtration, nano-filtration, reverse osmosis or pervaporation or a combination thereof. By this selection different kinds of recycle products are obtainable.

According to one aspect of the present invention, the water and water soluble organics after the second separation step may be transformed into drinkable water in a process of reverse osmosis. By the method comprising the process of reverse osmosis one very usable recyclable product is obtained.

According to one aspect of the present invention, the water soluble organic may comprising up-concentrated methanol may be re-circulated to the pre-treating step. A further optimization of the converting method is hereby obtained, and the converted product of up-concentrated methanol is reused.

Additionally, the method may according to one aspect of the invention comprise a phase separator, whereby separation of oil as product is obtained.

According to one aspect of the present invention, the step of contacting the residual product in the fluid with a heterogeneous catalyst may be performed while the temperature is kept substantially constant. By keeping the temperature constant in the contacting step the contacting of the fluid with the heterogeneous catalyst is kept in the same condition and the conversion is therefore constant throughout the contacting step. A further advantage is that the equilibriums and reaction rates of the chemical reactions involved in the conversion are kept constant throughout the contacting step, thereby ensuring uniformity in the products formed by the conversion.

In another aspect of the present invention, the temperature in the step of contacting may be in the range 200-650° C., such as in the range 200-450° C., and preferably in the range 200-374° C., and even more preferably in the range 250-374° C., such as in the range 275-350° C. By keeping these low temperatures the conversion process is using less energy in converting the same amount of residual product than at higher temperatures. A low temperature together with a pH value above 7 decreases the corrosion of the materials used for the apparatus in which the present method is performed.

A low temperature in the contacting step increases the fraction of the residual product being converted into hydrocarbon fuels, and thereby the oil production capacity of the contacting step. At such low temperatures the solubility of salts is high compared to higher temperature whereby the conversion process is further advantageous due to almost no salts depositing occurs inside the apparatus. Furthermore, at such low temperatures the residual product is less converted into soot and tar, which products are not very recyclable. Finally such low temperature allows construction of the apparatus from less corrosion resistant materials, further improving the competitive.

According to another aspect of the present invention, the pressure for said conversion may be in the range 225-600 bars, such as in the range 225-400 bars and preferably in the range 225-350 bars, such as in the range 240-300 bars. By using pressures inside these ranges it is obtained that standard components and equipment may be used for the present method whereby the cost of the conversion process and apparatus is substantially decreased compared to the same at higher pressures.

Furthermore, the method may according to the invention further comprise the step of contacting is done in less than 30 minutes, such as less than 20 minutes, preferably less 10 minutes, such as less than 7.5 minutes, and even more preferably in the range 0.5-6 minutes, such as in the range 1-5 minutes. By contacting the fluid at in a short period the conversion process time is decreased without decreasing the conversion processing of residual product substantially.

Additionally, the compound of at least one element of group IVB of the periodic table may comprise zirconium and/or titanium according to another aspect of the present invention. By using zirconium and/or titanium as a heterogeneous catalyst the conversion process time is decreased without decreasing the conversion processing of organic material.

In another aspect of the present invention the compound of at least one element of group IVB of the periodic table may be on an oxide and/or hydroxide form or a combination of the two. By using the heterogeneous catalyst on an oxide and/or hydroxide form the conversion process time is decreased without decreasing the conversion processing of organic material.

Advantageously, the compound of at least one element of group IVB of the periodic table is at least partly on a sulphate or sulphide form according to another aspect of the present invention. By using the heterogeneous catalyst on a sulphate or sulphide form the conversion process time is decreased without decreasing the conversion processing of organic material.

According to one aspect of the present invention, the heterogeneous catalyst may further comprise at least one element selected from the group consisting of Fe, Ni, Co, Cu, Cr, W, Mn, Mo, V, Sn, Zn, Si in an amount up to 20% by weight, such as an amount up to 10% by weight, preferably in an amount up to 5% by weight, such as up to 2.5% by weight. By using the aforementioned heterogeneous catalyst together with one or more elements of this group the conversion process time is substantially decreased without decreasing the conversion processing of organic material.

Furthermore, these elements may be on an oxide and/or hydroxide form according to another aspect of the present invention, whereby the conversion process time is further decreased without decreasing the conversion processing of organic material.

In yet another aspect of the present invention said heterogeneous catalyst may be in the form of suspended particles, tablets, pellets, rings, cylinders, a honey comb structure, a fibrous structure and/or a combination of these. The advantage of said heterogeneous catalyst structures is to control the flow distribution of the residual product stream being contacted with the catalyst, while ensuring reasonable pressure drop and contact to all of the catalyst surface.

Additionally, said heterogeneous catalyst is at least partly contained in a reactor according to another aspect of the present invention. It is hereby possible to reuse that part of the catalyst, which is inside the reactor.

Advantageously, said reactor is a fixed bed reactor according to another aspect of the present invention. By using a fixed bed reactor, it is hereby possible to even more easily reuse that part of the catalyst, which is inside the reactor.

According to one aspect of the present invention, said heterogeneous catalyst may have a BET surface area of at least 10 m2/g, such as 25 m2/g, and preferably at least 50 m2/g, such as 100 m2/g, and even more preferably at least 150 m2/g, such as at least 200 m2/g. By having this BET surface area, the conversion process time is further decreased without decreasing the quality of the conversion process, as sufficient catalytic active surface area is ensured.

According to another aspect of the present invention, said heterogeneous catalyst may comprise at least one surface area stabilizer selected from the group consisting of Si, La, Y or Ce or a combination thereof. By having this surface stabilizer, the catalyst service lifetime time is further expanded without decreasing the quality of the conversion process.

Advantageously, said heterogeneous catalyst may according to one aspect of the present invention comprise said at least one surface area stabilizer in an effective amount up to 20% by weight, such as an effective amount up to 10% by weight, preferably said surface area stabilizers in an effective amount up to 7.5% by weight, such as surface stabilizers in an effective amount up to 5% by weight, and more preferably said surface stabilizers are present in an effective amount from 0.5-5% by weight, such as 1-3% by weight. By having this surface stabilizer in up to 20% by weight, the catalyst service lifetime is further expanded without decreasing the quality of the conversion process.

In yet another aspect of the present invention said heterogeneous catalyst may have a BET surface area of at least 10 m2/g after 1000 hours of use, such as BET surface area of at least 25 m2/g after 1000 hours of use, and preferably a BET surface area of at least 50 m2/g after 1000 hours of use, such as a BET surface area of at 100 m2/g after 1000 hours of use, and even more preferably a BET surface area of at least 150 m2/g after 1000 hours in use, such as at a BET surface area of least 200 m2/g after 1000 hours in use. By having this BET surface area of at least 10 m2/g after 1000 hours of use, the conversion process time is further decreased without decreasing the quality of the conversion process, as sufficient catalytic active surface area is ensured.

Furthermore, said heterogeneous catalyst is produced from red mud according to another aspect of the present invention. It is hereby obtained to use waste product in the converting of the organic material, which also is a waste product.

Additionally, the method may according to the invention further comprise the step of re-circulating carbonates and/or hydrogen carbonates. By re-circulating carbonates and/or hydrogen carbonates the method is reusing products resulting from the conversion method and an optimizing of the method is hereby obtained.

The concentration of said carbonates and/or hydrogen carbonates may according to an aspect of the invention be at least 0.5% by weight, such as at least 1% by weight, and preferably at least 2% by weight, such as at least 3% by weight, and more preferably at least 4% by weight, such as at least 5% by weight. The carbonates and bicarbonates are important activators in the catalytic conversion performed by the homogenous catalyst.

Furthermore, the method may according to the invention further comprise the step of re-circulating at least one alcohol. By re-circulating at least one alcohol the method is reusing products resulting from the conversion method and an optimizing of the method is hereby obtained.

According to one aspect of the present invention, said at least one alcohol may comprise methanol, whereby a very usable recyclable product is reused in optimizing the method.

According to another aspect of the present invention, the methanol content in said fluid may be at least 0.05% by weight, such as at least 0.1% by weight, and preferably at least 0.2% by weight, such as at least 0.3% by weight, and even more preferably at least 0.5% methanol by weight, such as at least 1% by weight. Methanol is involved in the chemical reactions responsible for producing the oil product, and in the chemical reactions destroying the radicals otherwise responsible for formation of soot and tar during the decomposition of the organic material.

Advantageously, the method may according to another aspect of the present invention comprise the step of re-circulating a fluid containing hydrogen. By re-circulating a fluid containing hydrogen the method is reusing products resulting from the conversion method and an optimizing of the method is hereby obtained.

In yet another aspect of the present invention the hydrogen content of said fluid corresponds to at least 0.001% by weight of the amount of said residual product to be treated, such as at least 0.01% by weight of the amount of said residual product to be treated, and preferably 0.1% by weight of the amount of said residual product to be treated, such as 0.2% by weight of the amount of said residual product to be treated, and even more preferably the hydrogen content of the fluid is at least 0.5% by weight of the amount of said residual product to be treated, such as at least 1% by weight of the amount of said residual product to be treated. Hydrogen is involved in the chemical reactions producing saturated oil compounds, and in the reactions destroying free radicals, otherwise leading to formation of soot and tar during the thermal decomposition of the residual product during the conversion.

Furthermore, the method may according to the invention further comprise the step of re-circulating at least one carboxylic acid. By re-circulating at least one carboxylic acid the method is reusing products resulting from the conversion method and an optimizing of the method is hereby obtained.

Additionally, said at least one carboxylic acid may comprise at least one carboxylic acid having a chain length corresponding to 1-4 carbon atoms according to another aspect of the present invention. The said at least one carboxylic acid corresponding to 1-4 carbon atoms is involved in the chemical chain formation reactions producing the oil product.

Furthermore, said at least one carboxylic acid may comprise formic acid and/or acetic acid according to another aspect of the present invention. The said at least one carboxylic acid corresponding to 1-4 carbon atoms is involved in the chemical chain formation reactions producing the oil product.

Advantageously, the concentration of said carboxylic acid(s) in said fluid may according to the present invention be at least 100 part per million by weight, such as at least 250 part per million by weight, and preferably at least 400 parts per million by weight, such as at least 500 parts per million by weight. At this concentration level the oil product producing chemical reactions rates are sufficient to ensure conversion of the residual product to said oil product.

In one aspect of the present invention the method may comprise the step of re-circulating at least one aldehyde and/or at least one ketone. By re-circulating at least one aldehyde and/or at least one ketone the method is reusing products resulting from the conversion method and an optimizing of the method is hereby obtained.

In another aspect of the present invention said at least one aldehyde and/or at least one ketone comprises at least one aldehyde and/or at least one ketone having a chain length corresponding to 1-4 carbon atoms. The said at least one aldehyde or ketone corresponding to 1-4 carbon atoms is involved in the chemical chain formation reactions producing the oil product.

In yet another aspect of the present invention said at least one aldehyde and/or at least one ketone comprises formaldehyde and/or acetaldehyde. The said at least one aldehyde or ketone corresponding to 1-4 carbon atoms is involved in the chemical chain formation reactions producing the oil product.

According to the present invention, the concentration of said at least one aldehyde and/or at least one ketone in said fluid may be at least 100 part per million by weight, such as at least 250 part per million by weight, and preferably at least 400 parts per million by weight, such as at least 500 parts per million by weight. At this concentration level the oil product producing chemical reactions rates are sufficient to ensure conversion of the residual product to said oil product.

Advantageously, the homogeneous catalyst comprises potassium and/or sodium according to one aspect of the present invention. By using potassium and/or sodium as a homogeneous catalyst the conversion process time is decreased without decreasing the conversion processing of organic material, and the rates chemical reactions involved in the oil product formation are enhanced to facilitate production of said oil product.

Furthermore, according to another aspect of the present invention the homogeneous catalyst may comprise one or more water soluble salts selected from the group consisting of KOH, $K_2CO_3$, $KHCO_3$, NaOH, $Na_2CO_3$ or $NaHCO_3$ or a combination thereof. In combination with the carbon dioxide formed as part of the conversion of the residual product said salts are converted into the carbonate involved in the chemical reactions as activator.

In another aspect of the present invention the concentration of the homogeneous catalyst may be at least 0.5% by weight, such as at least 1% by weight, and preferably at least 1.5% by weight, such as at least 2.0% by weight, and even more preferably above 2.5% by weight, such as at least 4% by weight. At this concentration level the oil product producing chemical reactions rates are sufficient to ensure conversion of the residual product to said oil product.

Additionally, said fluid comprises water according to another aspect of the present invention. Water is a cheap an very frequent fluid and therefore by using water the cost to method of converting residual product is kept to a minimum and the method may be used in all areas of the world.

According to one aspect of the present invention, said water may have a concentration of at least 5% by weight, such as at least 10% by weight, and preferably at least 20% by weight, such as at least 30% by weight, and even more preferably at least 40% by weight. The residual product to be converted must be pumpeable.

The concentration of said water in said fluid may according to another aspect of the present invention be up to 99.5% by weight, such as up to 98% by weight, and preferably up to 95% by weight, such as up to 90% by weight, and even more preferably up to 85% by weight, such as up to 80% by weight. By decreasing the water content the heat value of the feedstock is increased, leading to increased oil production capacity at constant processing cost, without sacrificing the pumpability of the residual product to be converted.

In one aspect of the present invention said at least one carbonate and/or at least one hydrogen carbonate and/or at least one alcohol and/or at least one carboxylic acid and/or at least one aldehyde and/or at least one ketone may at least partly be produced by the conversion of said residual product. By reusing a product resulting from the conversion process, the conversion process time is decreased without decreasing the conversion processing of organic material. Furthermore expenses for treating an effluent stream are saved.

In another aspect of the present invention said at least one carbonate and/or at least one hydrogen carbonate and/or at least one alcohol and/or at least one carboxylic acid and/or at least one aldehyde and/or at least one ketone may be re-circulated after the step of contacting. It is hereby obtained that some of the resulting products from the conversion process is reused and that the conversion process time is decreased without decreasing the conversion processing of organic material.

Furthermore, at least part of a stream of said recirculation may according to another aspect of the present invention be mixed in a ratio with a feed stream of said fluid comprising said homogeneous catalyst and residual product to be converted before entering the catalytic reactor. It is hereby obtained that some of the resulting products from the conversion process is reused and that the conversion process time is decreased without decreasing the conversion processing of organic material.

Additionally, the ratio of the re-circulating stream to the feed stream of said fluid may according to another aspect of the present invention be in the range 1-20, such as 1-10, and preferably within the range 1.5-7.5, such as in the range 2-6, and more preferably in the range 2.5-5 by mass/volume. It is hereby obtained that some of the resulting products from the conversion process is reused and that the conversion process time is decreased without decreasing the conversion processing of organic material.

Advantageously, the conversion of said residual product may according to another aspect of the present invention be at least 90%, such as at least 95%, and preferably above 97.5%, such as above 99%, and even more preferably above 99.5%, such as above 99.9%. The high conversion leads to maximization of the oil production capacity, and minimizes or eliminates the content of unconverted residual product in oil product and mineral product, thereby eliminating the need for a separation step.

According to one aspect of the present invention said reactor with heterogeneous catalyst may be subjected to a treatment with hot pressurised water at pre-selected intervals.

According to another aspect of the present invention, said treatment with hot pressurised water may have a duration of less than 12 hours, such as a duration of less than 6 hours, preferably a duration of less than 3 hours, such as a duration of less than 1 hour.

In another aspect of the present invention the interval between such treatment with hot pressurised water may be at least 6 hours, such as at least 12 hours, preferably said interval between such treatment with hot pressurised water is at least 24 hours, such as at least one week.

By treating or flushing the reactor with hot pressurised water, the life time of the reactor is increased and the cost of the method is thereby substantially decreased.

In yet another aspect of the present invention said residual product may be selected from the group consisting of sludge, such as sewage sludge, liquid manure, corn silage, clarifier sludge, black liquor, residues from fermentation, residues from juice production, residues from edible oil production, residues from fruit and vegetable processing, residues from food and drink production, leachate or seepage water or a combination thereof.

According to one aspect of the present invention, said residual product may comprise a lignocelulotic materials, selected from the group consisting of biomass, straw, grasses, stems, wood, bagasse, wine trash, sawdust, wood chips or energy crops or a combination thereof.

According to another aspect of the present invention, said residual product may comprise a waste, such as house hold waste, municipal solid waste, paper waste, auto shredder waste, plastics, polymers, rubbers, scrap tires, cable wastes, CCA treated wood, halogenated organic compounds, PCB bearing transformer oils, electrolytic capacitors, halones, medical waste, risk material from meat processing, meat and bone meal, liquid streams, such as process or waste water streams containing dissolved and/or suspended organic material.

Advantageously, said sludge may according to another aspect of the present invention be sludge from a biological treatment process.

According to one aspect of the present invention said residual product may be sludge from a waste water treatment process.

In another aspect of the present invention said biological treatment process may be part of a waste water treatment process.

Furthermore, said biological water treatment process may according to another aspect of the present invention be an aerobic process.

Additionally, said biological water treatment process may be an anaerobic process according to another aspect of the present invention.

The method is capable of converting many kinds of residual product as mentioned above. Even though the method is performed at a relatively low temperature and a relatively low pressure the temperature and pressure is still sufficient to disinfect the resulting product. Which means regardless what residual product the resulting products is usable without infecting risk, e.g. residues from residues from food production, such as meat from a cow or a veal will not result in the spreading of the disease BSE. Likewise will virus, bacteria etc. from the residual product not be spread in a subsequent use of the resulting products.

Advantageously, said residual product may have been subjected to a mechanical dewatering according to another aspect of the present invention. By dewatering the residual product the heat value of the feedstock is increased, leading to increased oil production capacity at constant processing cost, without sacrificing the pumpability of the residual product to be converted.

Furthermore, said mechanically dewatered residual product may according to another aspect of the present invention have a dry solid content of at least 10% by weight, preferably at least 15% by weight, more preferably at least 20% by weight, most preferred 25% by weight.

By the pre-treatment step of the method it is obtained to increase the dry solid content, which again decreases the conversion process time.

Additionally, said residual product may according to another aspect of the present invention comprise a mixture of sludge, lignocelulotic materials or waste.

In another aspect of the present invention the concentration of said residual product in said fluid may be at least 5% by weight, such as at least 10% by weight, preferably the concentration of said residual product is at least 15% by weight, such as at least 200% by weight, and more preferably the concentration of said residual product is at least 30% by weight, such as at least 50% by weight.

Advantageously, the elements of group IA of the periodic table may be ash obtained from combustion of biomass or ash from coal firing according to another aspect of the present invention.

In preferred embodiments of the method according to the present invention the heating may advantageously be performed at least partly by microwave heating.

By mixing the different organic materials it is obtained that less catalyst has to used in the further processing and/or that the rate of the processing time is increased.

In a further aspect of the present invention, a method for a converting residual product, preferably being residual product according to the other aspect of the invention, into hydrocarbon fuels. The method preferably comprises the steps of:

pressurizing said residual product being in a fluid to a pressure of above 150 bar heating said material to a temperature of above 110° C. at least partly microwave heating.

The microwave heating of said residual product in said fluid to a temperature above 110° C. may preferably be performed in the presence of a homogeneous catalyst comprising a compound of at least one element of group IA of the periodic table of elements, Alternatively or in combination therewith, the method may further comprise contacting said residual product in said fluid with a heterogeneous catalyst comprising a compound of at least one element of group IVB of the periodic table and/or alpha-alumina and/or a zeolite. The temperature of the microwave heating may preferably be substantially the same as in the pretreatment step, such as in the range 110-150° C. In preferred embodiments, the maximum temperature may preferably be below 300° C. such as below 275° C., and preferably below 250° C. such as below 225° C., and even more preferably below 200° C., such as below 175° C.

The present invention further relates to the product obtained by the aforementioned method. Said product may according to the present invention comprise hydrocarbon in the form of oil. A resulting product which is very usable is hereby obtained in that oil is presently a very demanded product all over the world. A product such as oil is possible to obtain in that the method is performed at very low temperatures.

In another aspect of the present invention said fluid may have a feed carbon content and a feed hydrocarbon content, where the hydrocarbon oil product comprises at least 20% of the feed carbon content, such as at least 35% of the feed hydrocarbon content, preferably comprises said hydrocarbon oil product at least 50% of the feed carbon content, such as at least 65% of the feed carbon content and more preferably said hydrocarbon oil product comprises at least 80% of the feed carbon content.

In another aspect of the present invention at least 20% of a energy content in the feed stream may be recovered in said hydrocarbon oil product, such as at least 35% of the energy content, preferably is at least 50% of the energy content in the feed recovered in said hydrocarbon oil product, such as at least 65% of the feed energy content and even more preferable at least 80% of said feed energy content is recovered in said hydrocarbon oil product.

Furthermore, said hydrocarbon oil product comprises hydrocarbons with 12 to 16 carbon atoms according to another aspect of the present invention.

Advantageously, said hydrocarbon oil product may be substantially free of sulphur according to another aspect of the present invention.

Additionally, said hydrocarbon oil product may be substantially free of halogens according to another aspect of the present invention.

By the method according to the present invention a hydrocarbon oil product free of sulphur and/or halogens is hereby obtained. Such oils free of sulphur and/or halogens are very recyclable into new forms of energy without polluting the surroundings with reactions caused by sulphur and/or halogens.

Said hydrocarbon oil product may according to one aspect of the present invention comprise fatty acid esters and/or fatty acid methyl esters. The oxygen content of the fatty acid esters and methyl esters is known to improve the properties of the hydrocarbon oil as transportation fuel, due to the reduced particle emission from the combustion of the fuel.

The hydrocarbon oil product may have diesel-like properties according to another aspect of the present invention. The diesel-like hydrocarbon fuel might be mixed directly into conventional diesel oil, thereby saving the cost of refining the oil product.

Furthermore, the hydrocarbon oil product may have a oxygen content in the range 0.1-30% according to another aspect of the present invention. The oxygen content of the hydrocarbon fuel is known to improve the properties as transportation fuel, due to the reduced particle emission from the combustion of the fuel.

Additionally, the hydrocarbon oil product may be adsorbed on the surface of a mineral product according to another aspect of the present invention. This oil containing mineral product is an improved starting material for molten mineral processing processes.

The hydrocarbon product may also comprise methanol according to another aspect of the present invention. By further separation a purified methanol product might be obtained, which is preferred fuel for fuel cells or additive to gasoline for production of sustainable transportation fuels.

In another aspect of the present invention said hydrocarbon product comprising methanol may comprise at least 20% of the feed carbon content, such as at least 35% of the feed carbon content, preferably comprises said methanol product at least 50% of the feed carbon content, such as at least 65% of the feed carbon content and more preferably comprises said methanol product at least 80% of the feed carbon content. By further separation a purified methanol product might be obtained, which is preferred fuel for fuel cells or additive to gasoline for production of sustainable transportation fuels.

In yet another aspect of the present invention at least 20% of the energy content in the feed may be recovered in said hydrocarbon product comprising methanol, such as at least 35% of the energy content in the feed is recovered in said hydrocarbon product comprising methanol, preferably is at least 50% of the energy content in the feed recovered in said hydrocarbon product comprising methanol, such as at least 65% of the feed energy content is recovered in said hydrocarbon product comprising methanol and more preferably is at least 80% of said feed energy content recovered in said hydrocarbon product comprising methanol. By further separation a purified methanol product might be obtained, which is preferred fuel for fuel cells or additive to gasoline for production of sustainable transportation fuels.

The present invention further relates to the use of the aforementioned product for driving a engine or generator, for power production in an oil fired power plant, for process heating or domestic heating. These are all means of producing energy from a sustainable source, yet without having to replace or renew the hardware installations or infrastructure established for energy production from fossil fuels.

Furthermore, the present invention relates to the use of the aforementioned product as a blending component in petro-diesel or gasoline or in a suspension fired system or in a process for molten mineral processing. These are all means of producing energy from a sustainable source, yet without having to replace or renew the hardware installations or infrastructure established for energy production from fossil fuels.

Additionally, the present invention relates to the use of the aforementioned for producing a fertilizer product or for producing clean water stream. Said clean water stream may furthermore have drinking water quality.

The present invention additionally relates to an apparatus for converting a residual product into hydrocarbons, comprising:

a conversion system and a product recovery system, said conversion system comprises a first heating unit for heating a feed of fluid comprising organic material, preferably being a residual product according to the present invention, a catalyst reactor for contacting the feed of fluid comprising organic material, preferably being a residual product according to the present invention, with a heterogeneous catalyst, and an adjusting unit for adjusting the fluid to have a pH value of above 7, and said product recovery system comprises a separation unit, such as a—filter, preferably being a membrane-filter for separating out a first stream of oils and a second stream of water and water soluble organics, preferably water soluble salts being separated out to the first and/or the second stream.

The conversion system may also be termed a pre-conversion system as further conversion process may be applied.

According to one aspect of the present invention, the conversion system may further comprise a storage for feeding residual product to the fluid in a feeding direction.

Furthermore, the conversion system may further comprise a pre-treating unit situated after the feedstock and before the first heating unit in the feeding direction, according to another aspect of the present invention. By pre-treating the fluid comprising the residual product it is possible to increase the amount of solid-state material in the fluid, which again leads to a higher rate of conversion and thereby a higher production capacity. This results in a more efficient and cost saving converting of organic material.

Additionally, the conversion system may according to the present invention further comprise a first particle separating unit situated after the first heating unit in the feeding direction. By separating particles before contacting the fluid comprising the residual product with the heterogeneous catalyst the product resulting from the conversion process, such as oil, is then substantially free of being bound to these particles and therefore much more reusable straight after this conversion process. A second process, such as an refinery is thereby dispensable.

Said conversion system may according to the invention further comprise a second heating unit situated after the first particle separating unit and before the catalyst reactor in the feeding direction. It is hereby possible to optimize the temperature before entering the fluid into the reactor and thereby an optimization of the conversion process.

In another aspect of the present invention the conversion system may further comprise a second particle separation unit after the catalyst reactor in the feeding direction. This particle separating unit is for the same reason as above advantageous.

In yet another aspect of the present invention the conversion system may further comprise means for re-circulating part of the feed of fluid after the catalyst reactor into the feed of fluid before the second heating unit in the feeding direction. It is hereby obtained that some of the resulting products from the conversion process is reused and that the conversion process time is decreased without decreasing the conversion processing of organic material.

Furthermore, the first heating unit may according to the present invention comprise a first heat exchanger, which besides heating cools the fluid from conversion system before entering the product recovery system. It is hereby obtained to reuse energy inside the apparatus and thereby same energy in the total amount of energy used in converting the organic material.

Additionally, the pre-treating unit may according to the invention further comprise a heat exchanger, which besides heating the fluid in the pre-treating system cools the fluid from conversion system before entering the product recovery system. This heat exchanger is for the same reason as above advantageous The pre-treating unit may further comprise a first expansion unit, which is situated between the first heat exchanger and the second heat exchanger, according to an aspect of the present invention. It is hereby obtained to produce gas, such as fuel gas.

In one aspect of the present invention the product recovery system may further comprise a gas separating unit for separation of gas, such as fuel gas, the gas separating unit is situated after the second heat exchanger and before the first separation unit, preferably being a membrane-filter in the feeding direction. It is hereby obtained to separate the aforementioned gas, such as fuel gas from the rest of the fluid.

In another aspect of the present invention the product recovery system may further comprise means for re-circulating said gas, such as fuel gas for heating the fluid in the second heating unit. It is hereby obtained that some of the resulting products from the conversion process is reused and that the conversion process time is decreased without decreasing the conversion processing of organic material.

In yet another aspect of the present invention the product recovery system may further comprise a second expansion unit situated after the first separation unit, preferably being a membrane-filter in the feeding direction. It is hereby obtained to produce oil out from the fluid, and thereby a very Furthermore, the product recovery system may according to one aspect of the present invention further comprise a phase separator unit for separation of oil from the first stream, said phase separator unit is situated after the separation unit, preferably being membrane-filter in the feeding direction. It is hereby obtained to separate oil from the fluid.

Additionally, the product recovery system may according to another aspect of the present invention further comprises means for re-circulating part of the first stream into the pre-treating unit of the conversion system. It is hereby obtained that some of the resulting products from the conversion process is reused and that the conversion process time is decreased without decreasing the conversion processing of organic material.

Advantageously, the product recovery system may according to another aspect of the present invention further comprise direct methanol fuel cell for generating electricity from the second stream.

According to yet another aspect of the present invention the product recovery system further comprises one or more separation units may be selected from the group of phase separators, centrifuges, membrane processes comprising ultra-filtration, nano-filtration, reverse osmosis or pervaporation or a combination thereof.

Furthermore, the product recovery system may according to an aspect of the invention further comprise a second separation unit, such as a second membrane-filter for separating a purified methanol compound from the second stream.

In another aspect of the present invention the product recovery system may further comprise means for re-circulating the purified methanol compound from the second stream to the pre-treating unit of the conversion system. It is hereby obtained that some of the resulting products from the conversion process is reused and that the conversion process time is decreased without decreasing the conversion processing of organic material.

The present invention further relates to a plant comprising the aforementioned apparatus, for producing the aforementioned product by using the aforementioned method.

In one aspect of the present invention the plant may comprise means for supplying residual product to the apparatus and means for removal of the products from the apparatus.

In another aspect of the present invention the plant may further comprise a refinery The present invention further relates to a heterogeneous catalyst for use in a method for converting an residual product into hydrocarbons, comprising a compound of at least one element of group IVB of the periodic table and/or alpha-alumina.

Additionally, the compound of at least one element of group IVB of the periodic table may comprise zirconium and/or titanium according to an aspect of the present invention.

Furthermore, the compound of at least one element of group IVB of the periodic table may be on an oxide and/or hydroxide form or a combination of the two according to an aspect of the present invention.

Advantageously, the compound of at least one element of group IVB of the periodic table may be at least partly on a sulphate or sulphide form according to an aspect of the present invention.

In another aspect of the present invention the heterogeneous catalyst may further comprise at least one of element selected from group of Fe, Ni, Co, Cu, Cr, W, Mn, Mo, V, Sn, Zn, Si in an amount up to 20% by weight, such as an amount up to 10% by weight, preferably in an amount up to 5% by weight, such as up to 2.5% by weight.

Furthermore, these elements are on an oxide and/or hydroxide form according to another aspect of the present invention.

Additionally, the heterogeneous catalyst is in the form of suspended particles, tablets, pellets, rings, cylinders, a honeycomb structure and/or a combination of these according to yet another aspect of the present invention.

In yet another aspect of the present invention the heterogeneous catalyst may have a BET surface area of at least 10 m2/g, such as 25 m2/g, and preferably at least 50 m2/g, such as 100 m2/g, and even more preferably at least 150 m2/g, such as at least 200 m2/g.

Advantageously, the heterogeneous catalyst further comprises at least one surface area stabilizer selected from the group of Si, La, Y and/or Ce according to an aspect of the present invention.

Subsequently, the heterogeneous catalyst may according to an aspect of the present invention comprise said at least one surface area stabilizer in an effective amount up to 20% by weight, such as an effective amount up to 10% by weight, preferably said surface area stabilizers in an effective amount up to 7.5% by weight, such as surface stabilizers in an effective amount up to 5% by weight, and more preferably said surface stabilizers are present in an effective amount from 0.5-5% by weight, such as 1-3% by weight.

In another aspect of the present invention the heterogeneous catalyst may have a BET surface area of at least 10 m2/g after 1000 hours of use, such as BET surface area of at least 25 m2/g after 1000 hours of use, and preferably a BET surface area of at least 50 m2/g after 1000 hours of use, such as a BET surface area of at least 100 m2/g after 1000 hours of use, and even more preferably a BET surface area of at least 150 m2/g after 1000 hours in use, such as at a BET surface area of least 200 m2/g after 1000 hours in use.

Finally, the heterogeneous catalyst may be produced from red mud according to an aspect of the present invention.

DETAILED DESCRIPTION OF THE INVENTION

The present invention will in the following be described with reference to the accompanying drawings, in which.

The drawings are schematically and shown for the purpose of illustration.

Figure 1:
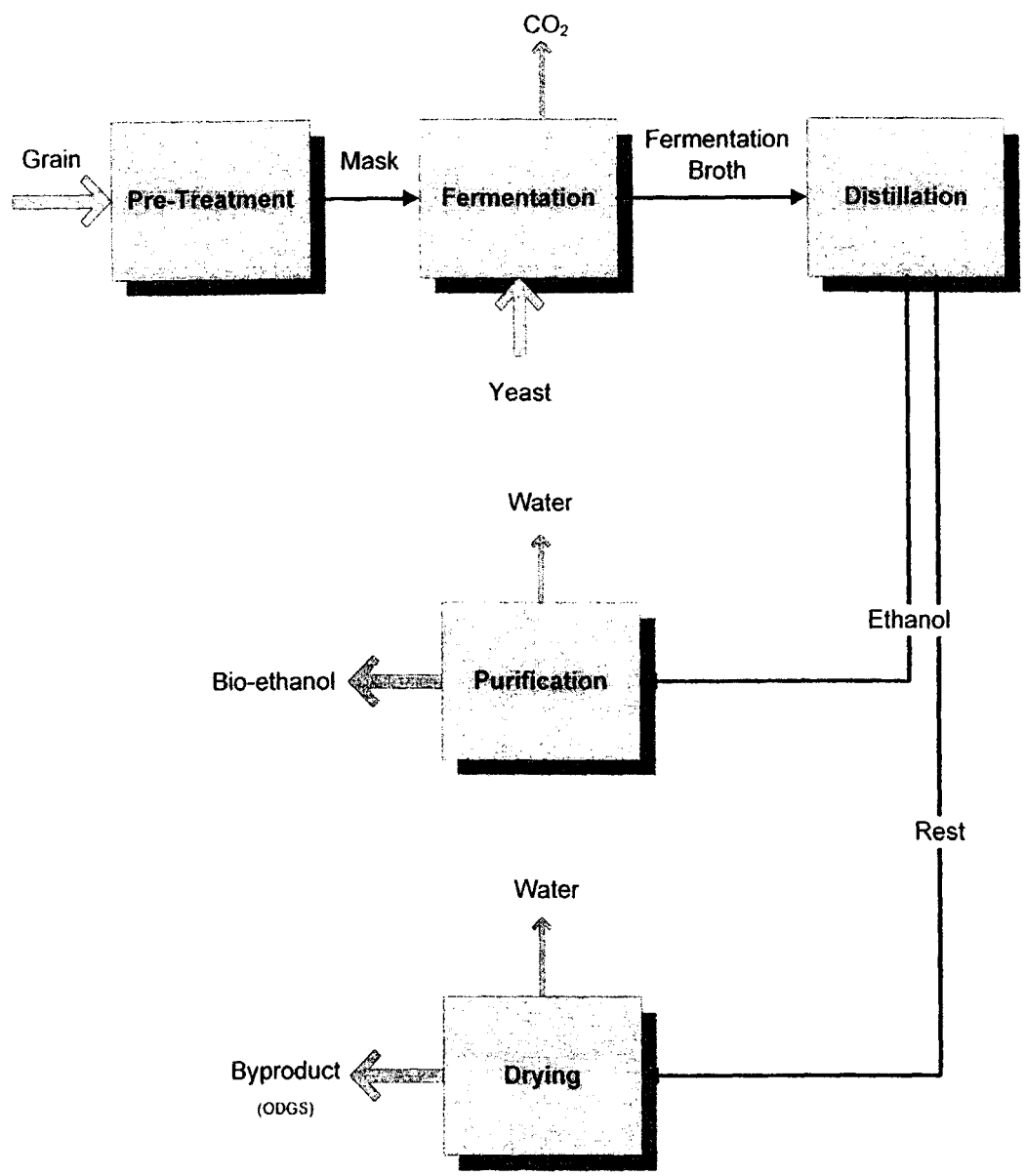
FIG. 1 shows a generalized flow sheet of a conventional bio-ethanol production.

FIG. 1 is an example of a conventional bio-ethanol production process. Bio-ethanol is conventionally produced by fermentation of grain, corn or other plant seeds, which are rich in starch. Only the seeds enter the bio-ethanol process, while the rest of plant is separated from the seeds and used for other purposes.

The bio-ethanol production process involves a quite complex chemical plant, as energy integration is the key to successful process design. The process comprises a number of unit operations, which may be organized into four main process steps:
1. Feedstock preparation
2. Fermentation
3. Bio-ethanol separation
4. Residual product upgrading The feedstock pre-treatment may include milling, in which the feedstock material is mechanically divided into smaller parts. Water may be added either before the milling (wet milling) or after the milling (dry milling) to produce a feed pulp. Normally the entire feedstock is processed, i.e. the feed pulp includes also the cellulostic and protein part of the seeds. Enzymes may be added to the pulp in the liquefaction step to break down the plant material structure by hydrolysis and liberate starch from the seeds. The starch is further hydrolysed to smaller sugars—dextrins. In a subsequent saccharification step dextrins may be broken down to low molecular weight sugars suitable for fermentation. The sacchairification may be performed by enzymatic hydrolysis using a mixture of enzymes.

One of the major energy consumptions in prior art methods are in the pre-treatment process, and hence in a preferred embodiment according to the present invention at least 50% of the energy required for said pre-treatment process being supplied by said energy distribution process, such as at least 70% of the energy required for said pre-treatment process being supplied by said energy distribution process, and preferably at least 80% of the energy required for said pre-treatment process being supplied by said energy distribution process, such as at least 90% of the energy required for said pre-treatment process being supplied by said energy distribution process, and even more preferably at least 95% of the energy required for said pre-treatment process being supplied by said energy distribution process, such as substantially of the energy required for said pre-treatment process being supplied by said energy distribution process.

The feed pulp is fermented ethanol by addition of yeast or by thermolabile microorganism such as thermolabile bacterias. Glucose and other low molecular weight sugars may be converted during the fermentation process, while all other organic parts of the feedstock are remaining unconverted in the fermentation broth. During fermentation carbon dioxide is liberated from the fermentation process.

The ethanol separation step includes distillation of the fermentation broth to separate an azeotropic ethanol/water mixture. Water may be removed from the mixture by zeolite molecular sieving or similar processes, producing almost water free bio-ethanol (99.9% pure).

The remaining fermentation broth, i.e. the distillation rest including unconverted starch, other organics from the feedstock like cellulostic material, proteins and other feedstock cell material as well as dead yeast cells, is processed to produce animal fodder. The processing includes numerous steps, including decanting and drying, to end with a dry material—Dried Distilled Grains with Solubles (DDGS), which is sold as animal fodder.

The main energy consumptions in the process are heating during liquefaction and saccharification, as these conversions are performed at elevated temperatures (65-110° C.), heat for the distillation performed at 80° C. and heat for regeneration of the molecular sieves used in the ethanol separation.

Figure 2:
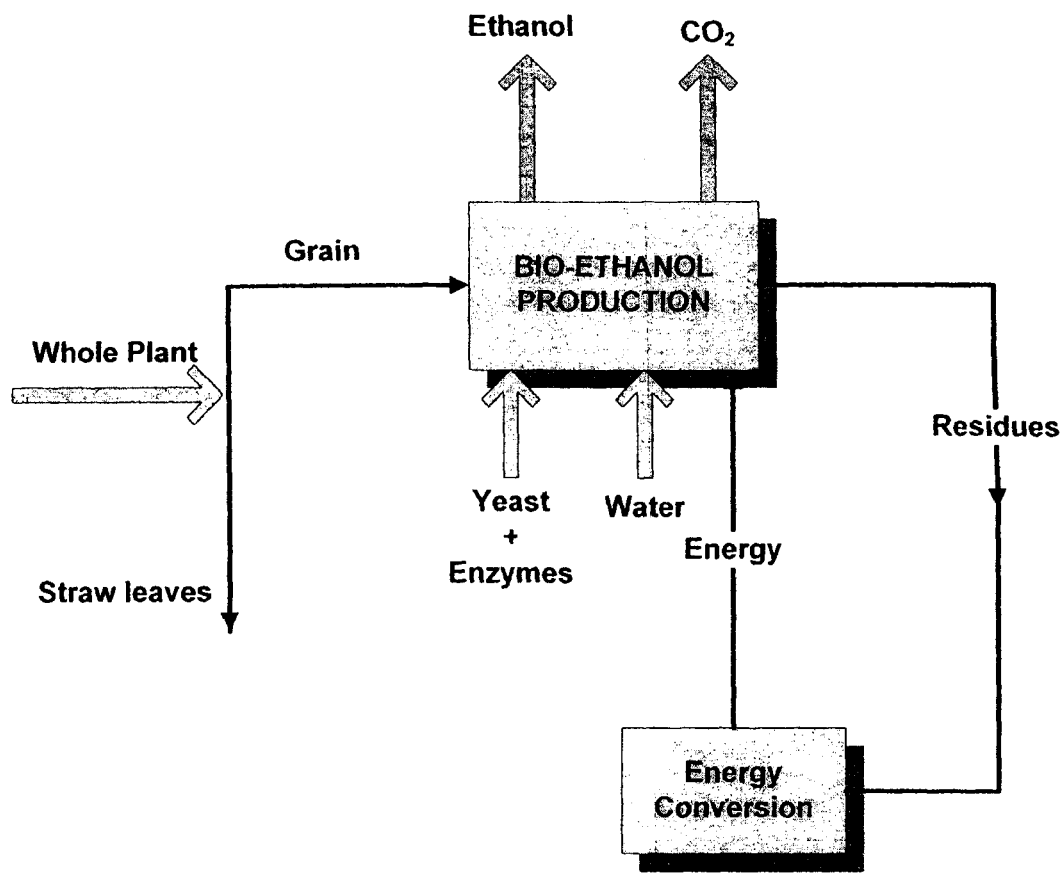
FIG. 2 shows a generalized flow sheet of an embodiment of a bio-ethanol production according to the present invention.
Figure 3:
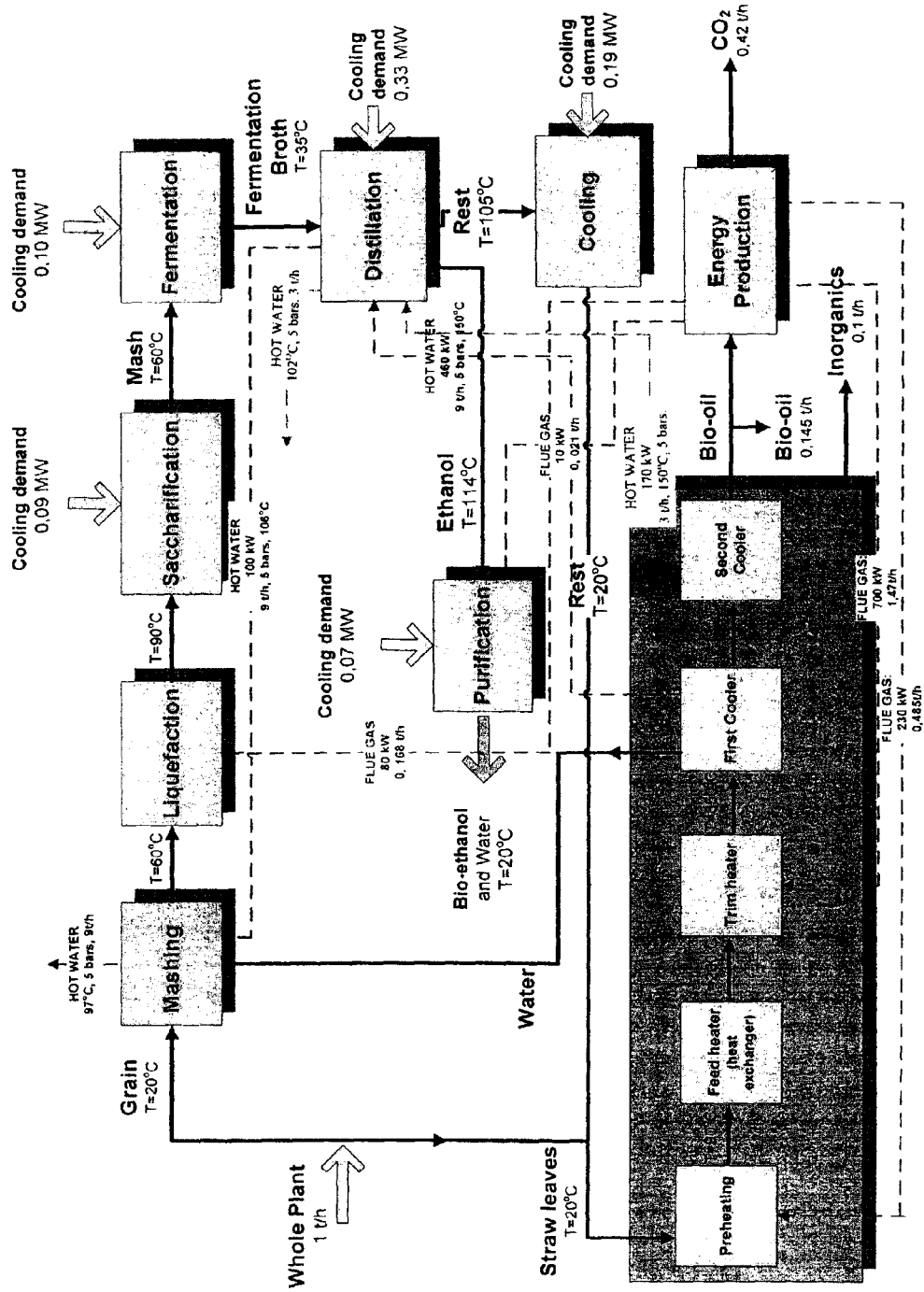
FIG. 3 shows a flow sheet of a preferred embodiment of a bio-ethanol production according to the present invention.

FIG. 2 is generalized flow sheet of an embodiment of a bio-ethanol production according to the present invention. Bio-ethanol is produced by the conventional process by fermentation of grains. But the wet residual product is used for energy production in an energy conversion step, as illustrated in FIG. 3. The produced energy may be used in the bio-ethanol production.

The energy conversion process may be, but is not limited to, conventional drying and combustion technologies, or biogas production. Further a number of new energy production technologies for conversion of the dried product are available, like hydrolysis and gasification. But particularly well suited methods for the energy conversion include high-pressure water based technologies such as supercritical water oxidation, supercritical wet gasification, hydrothermal upgrading or catalytic conversion in high pressure water.

FIG. 3 shows the energy distribution of a preferred embodiment of a bio-ethanol production according to the present invention. A feed stream of 1 t/h of plant material is harvested and fed into the process. The plant material is composed of 60% grains and 40% leaves and straw. The grain fraction contains 70% sugar, 10% of inorganics and 20% residual material that contains 80% carbon. The straw and leave ash/inorganics. Water in an amount of 4 times the amount of grain is added to grains. The grain fraction of the plant is introduced in the bio-ethanol process, where it is submitted to a pre-treatment step described in FIG. 1. This pre-treatment step comprises a milling unit operation and a liquefaction step. The liquefied starch-containing material is commonly called "mash".

Milling is used as pre-treatment to open up the material structure before the liquefaction. Two main processes are commonly used: wet and dry milling.

Wet milling gives a good separation of germ and starch granules and is mostly used when a parallel production of syrup is found in the process. It allows to separate the grain into its different fractions (starch, germ, fibers oil and protein) and to produce a variety of diverse co-products such as starch, corn oil.

In dry milling, the whole kernel is milled and used in the process. The ground meal is thereafter liquefied, saccharified and fermented to make ethanol. In this case, only ethanol and distilled grains are recovered.

In the following liquefaction step, the long chained starch-containing material is degraded (hydrolyzed) into maltodextrins (dextrins). Knowing that the starch containing material is heated to a temperature above the gelatinization temperature (above 85° C.), the liquefaction helps the handling by thinning the starch containing slurry, adding bacterial alpha-amylase (and also on a limited basis acid treatment). Liquefaction is usually carried out at temperatures around 105 to 110° C. for about 5-10 min, followed by a lower temperature holding period of about 1-2 hours at 95° C. The pH is maintained around 4.5-6.5 to avoid any bacterial growth. Different possible heating steps may be applied. A preliminary liquefaction step is usually carried out (80-85° C. and pH of 4 during 15 to 40 min with alpha amylases enzymes added to initiate the liquefaction) followed by jet cooking (temperature between 105-125° C. during 1-5 min) and a third liquefaction stage at 70-85° C. for 15-80 min (with addition of thermostable acid alpha-amylase that allows decreasing the fermentation time and increasing efficiency by reducing the residual starch left over during the fermentation).

In the following saccharification step, the maltodextrin contained in the mash is converted to low molecular sugars that can be metabolized by fermenting micro organisms in the fermentation stage. The saccharification is generally carried out enzymatically (using enzymes like glucoamylase, alpha-glucosidase, acid alpha-amylase), with temperatures around 30-65° C. (typically 60° C.), during 24 to 72 hours and pH around 4-6. It may be advantageous to add some nutrients (yeast extracts), salts (NaCl and ammonium sulfate) and other enzymes (cellulases, hemicellulase, xylanase . . . ) to the liquefied mash during saccharification.

In the following fermentation step, suitable fermenting micro organisms (yeast) convert sugars in the mash directly or indirectly into the fermentation products, preferably ethanol. Generally, the fermentation is ongoing for 24-96 hours and between 24-36° C., with pH around 4-5. The temperature and pH during fermentation are set to be suitable for the micro-organisms used. It may be advantageous to add some nutrients, salts (NaCl and ammonium sulfate) and enzymes (cellulases, hemicellulase) to the hydrolyzed starch and sugars during fermentation.

Saccharification may also be done simultaneously with fermentation. In this case, the enzymes and micro-organisms are added together. This simultaneous saccharification and fermentation process (SSF) is a widely used process in the ethanol production. The SSF process is usually conducted at temperatures above 34° C. in the presence of glucoamylase and thermo tolerant yeast. The advantage to carry out this step at elevated temperature is that less cooling is required after the initial liquefaction step (occurring at much higher temperature). Simultaneous liquefaction, saccharification and fermentation (LSF) are also found in industry. In a continuous fermentation process, the mash is flowing through several fermentation processes until the mash is fully fermented while in the batch case, the mash stays in one fermentor for an effective amount of time.

In the SSF process, a pre-saccharification step (1 to 4 hours) is usually done (before or simultaneously with the saccharification and fermentation steps), with temperature between 30 to 65° C. and pH around 4.5.

Distillation is thereafter performed on the fermentation broth from the fermentation step to recover the fermentation products (ethanol preferably). The fermentation and distillation steps may be carried out simultaneously or separately/sequentially.

After distillation, two products are recovered: Ethanol and a fermentation rest or residual product (whole stillage). The ethanol typically being an azeotropic mixture with water is further purified in the separation step by molecular sieving.

The fermentation rest or residual product is mixed with the straw and leaves from the plant, and introduced into a conversion process in high pressure water according to the present invention. The conversion process comprises a further pre-treatment process, a first heating process, a second heating process (trim heating), a reaction process (not shown), a first cooling process, a second cooling process, and a separation process. The conversion process is shown and described in more details in the FIGS. 5-9 below and in the illustrative examples. The conversion process converts the organics into hydrocarbons such as a bio-oil.

Part of the hydrocarbons are combusted in an energy production and energy is distributed to supply the energy consumptions in pre-treatment process (0.18 MW) and separation processes (0.63 MW) of the bio-ethanol production process. As the conventional dewatering process is eliminated and this typically consumes approximately the same amount of energy as the pre-treatment and separation processes, the energy consumption for bio-ethanol production has been significantly reduced.

Using all parts of the plant including straws and leaves, a process self-supplying with energy and having an overall positive energy balance is provided.

The bio-ethanol production may typically be substantially the same as in prior art methods (0.224 t/h), and addition here to a co-production of valuable hydrocarbons such as bio-oil (0.145 t/h) is enabled by the current invention.

Hence, the overall result is a more efficient process for production of bio-ethanol In the following a preferred embodiment of converting the residual product into energy and in particular in to a hydrocarbon fuel will be disclosed. The residual product contains among other species organic material.

Figure 4:
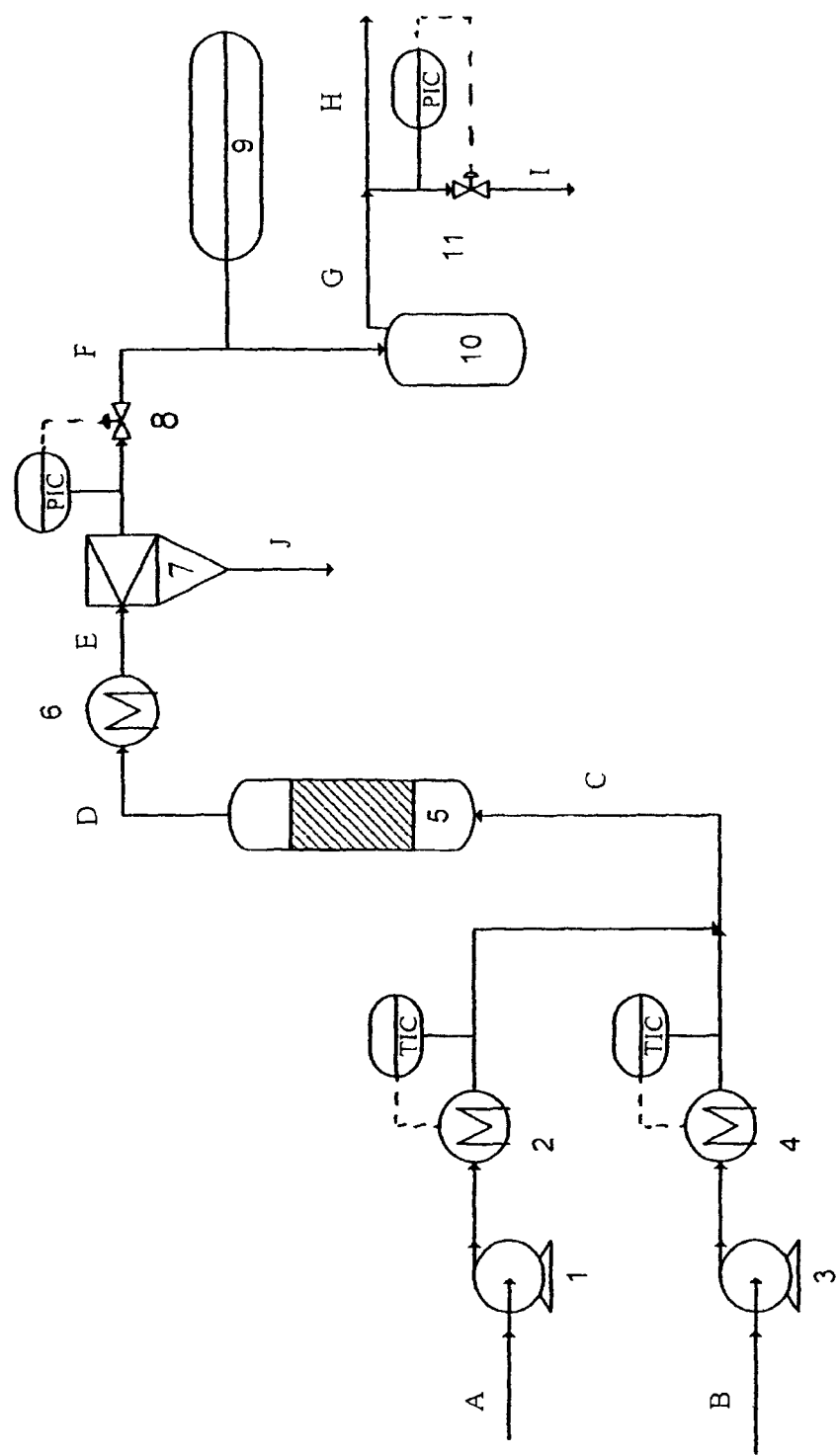
FIG. 4 shows a schematic drawing of laboratory scale set-up used for establishing the result described in the examples.

FIG. 4 is a schematic drawing of the laboratory set-up used for the tests given in the examples. The pre-treated fluid containing the homogeneous catalysts and organic material to be converted is supplied to the system at the position A. The fluid is pressurized by means of the pump 1 and is heated to approximately 230 C in the heater 2, comprising a heat exchanger and a temperature controller (TIC). A second fluid is supplied to the system at position B. This stream is pressurized by means of the pump 3 and heated in the heater 4, comprising a heat exchanger and a temperature controller (TIC), to the temperature necessary to obtain the desired conversion temperature of the mixed fluid streams at position 4. The heterogeneous catalyst is located in the tubular catalytic reactor 5. After contact with the heterogeneous catalyst, the fluid containing the converted organic material is cooled to ambient temperature in the cooler 6, and filtered in the filter 7 for separation and collection of suspended particles. Subsequently the fluid is expanded to ambient pressure over the valve 8. The system pressure is maintained by controlling the flow through 8, utilizing the pressure controller (PIC). The expanded fluid temperature is measured with the thermocouple 9. The liquid fraction of the stream is collected in a liquid trap 10, and the gas is vented off from the trap at position G. The flow rate and composition of the produced gas is continuously measured by a gas meter placed in H (not shown). The composition of the gas is analysed by gas chromatography (not shown) of a small sample taken through I, at controlled pressure established by the flow control valve and pressure controller (PIC) 11.

Figure 5:
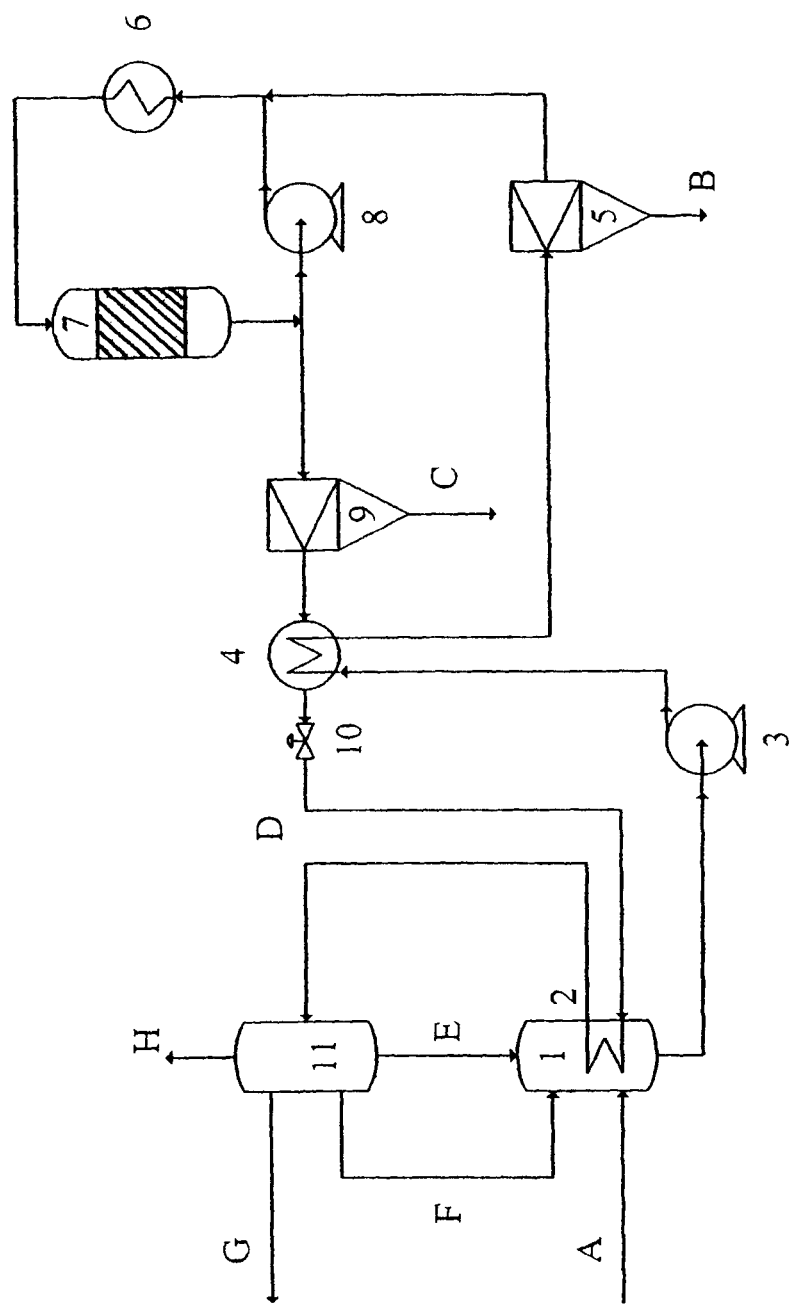
FIG. 5 shows a general process flow sheet of a preferred embodiment of the energy conversion step according to the present invention.

FIG. 5 shows a schematic drawing of a preferred aspect of a method according to the present invention. Organic material for conversion is received in a feed storage (not shown on the figure). Said organic material may comprise a wide range of biomass and wastes, and may also comprise fossil fuels such coal, shale, orimulsion, heavy fractions of crude oil etc. Many aspects according to the present invention involve treatment of organic material from a mixture of different sources of material as just mentioned.

The feed storage will typically have a capacity corresponding to three days of plant operation. The feed storage is preferably a concealed and agitated silo, such as an agitated concrete silo. A fluid containing the organic material is pumped to the pre-treatment step 1 at position A.

The first part of the pre-treatment comprises in this aspect a size reduction of the feed e.g. by cutting, grinding, milling and/or sieving the material. This size reduction may be an integral part of feeding pump (not shown). During the feeding operation to the pre-treatment the pressure of the fluid containing the organic material to be treated is increased to a pressure in the range 4-15 bars. In the second part of the pre-treatment the fluid containing said organic material is typically maintained in a pre-treatment vessel for a period of 0.5-2 hours. The pre-treatment vessel is preferably an agitated vessel, which is maintained at a temperature of 100-170 C, and preferably in the range 110 to 140 C. The energy for this pre-heating of said fluid comprising said organic material to be converted is preferably supplied, by recovering heat from one of the process streams to be cooled. In the figure this is illustrated by integrating the heat exchanger 2 in a vessel for recovery of heat from the process stream D.

The pH in the vessel is adjusted to a value above 7, and preferable in the range 8-10. This pH adjustment is in many aspects according to the present invention performed by adding additives to the vessel, e.g. by adding a base, which may also comprise an element of group IA of the periodic table. Non-limiting examples of such additives are KOH, NaOH, $K_2CO_3$, $Na_2CO_3$, ash from biomass or coal combustion. Such additives may be added to the vessel through the stream S.

During the residence in the pre-treatment vessel larger molecules such as cellulose, hemicellulose and lignin are hydrolyzed, and cells from biomass addition are opened facilitating the release of cell contents, such as salts. For a number of potential feedstock this cell opening involve release of catalysts such as potassium from the feedstock itself, thereby allowing for a very efficient process. A number of other additives may also enhance the pre-conversion of the organic material and are further advantageous for the subsequent processing. Such other additives include alcohols, such as methanol, carboxylic acids, aldehydes, and/or ketones. In a preferred aspect of the invention a number of such additives being utilized in the pre-treatment, are produced in-situ in the process and re-circulated to the pre-treatment step as shown by the streams E and F. Typical compositions of these recirculation streams is further described in relation to the FIGS. 6-8.

A fluid stream containing pre-converted organic material is withdrawn from pre-treatment vessel by the feed pump 3, and pressurized to the operating pressure e.g. 250 bars. The feed pump may comprise a plunger pump.

After pressurization the fluid containing the pre-converted organic material, the homogeneous catalyst and other additives is heated in the first heating step 4 by heat exchange with the hot converted product stream from the catalytic reactor. The temperature of the fluid containing the pre-converted organic material will in many applications according to the present invention be in the order of 20-30° C. below the operating temperature of the catalytic reactor. During this first heating step the organic material in the feed is further thermally decomposed. A number of undesirable side reactions may proceed during this thermal decomposition, such soot and char formation. Besides reducing the overall efficiency of the process, the may lead to operational problems such as plugging or reduced efficiency of heat exchanger, and deposition on downstream equipment. The aforementioned additives reduce these undesirable side reactions and enhance further the conversion of the organic material into desirable products.

From the heat exchanger 4, the fluid containing said pre-converted organic material may pass a first particle separation device 5 for collection of suspended particles, which may be formed during said pre-conversion during heat-up. This particles separation device 5 may comprise any conventional means for particle separation, e.g. a cyclone, a filter, a gravimetric settling chamber etc. Particles collected are withdrawn from the process shown by the stream B.

After the first particle separation device 5 the fluid containing said pre-converted organic material is mixed with a re-circulating stream from the catalytic reactor. This mixing will typically increase the temperature of the mixed fluid with 10-20 C, and the recirculation will further introduce desirable compounds for the further conversion into the feed. After mixing with the re-circulation stream the mixed fluid passes to a trim-heater (second heating unit) 6, wherein the temperature is raised to the operating temperature of the catalytic reactor 7. The trim-heater 6 may in many aspects according to the present invention be a gas or oil fired heater, and is preferably at least partly fuelled by re-circulating gas and/or other fuel products produced in the process. In a preferred aspect, this trimheater is fuelled by re-circulating the produced gas denoted I in FIG. 3. The re-circulation of said produced gas I may include a separation step.

In the catalytic reactor 7, the fluid containing homogeneous catalyst, additives, and pre-converted organic material is contacted with the heterogeneous catalyst. The heterogeneous catalyst will typically be contained in a tubular fixed bed, and the catalytic reactor may comprise multiple tubular fixed beds. During the conversion a dissolved fuel gas, a water soluble organics and an oil is generally produced. The product distribution is adjustable within a wide range of concentration of resulting products as shown in the examples below, and may be controlled by selecting a suitable combination of residence time, re-circulation flow rate, reaction temperature, and concentration of homogeneous catalyst and additives.

Part of the product stream from the catalytic reactor is re-circulated by the pump 8, and mixed with the fluid containing the pre-converted organic material as described above. The remaining part corresponding to the mass flow of the fluid containing the pre-converted organic material before mixing with the re-circulating stream is withdrawn to the second particle separation device 9. As for the first particle separation device this second particles separation device may comprise any conventional means for particle separation e.g. a cyclone, a filter, a gravimetric settling chamber etc. The main feature is to provide a hot separation of potential suspended particles produced oil prior to cooling and expansion to avoid adsorption of the oil to the suspended particles. However, in a number of applications of the present invention e.g. for feedstock with a low ash content this particle separation device may be optional. Particles collected in the second particle separation device are withdrawn from the process shown by the stream C.

Subsequent to the passage of the second particle separation device the fluid stream is cooled in by heat exchange with the feed stream in the heat exchanger 4, and in the heat exchanger 2 and expanded to a pressure in the range 75-225 bars over the expansion valve 10, and separated in the product recovery system 11. Some of the separated fluid stream from the product recovery system 11, such as the streams F and/or E may be re-circulated to the pre-treatment step as described above. The product recovery system 11 is further illustrated and described below in the FIGS. 6-9.

Figure 6:
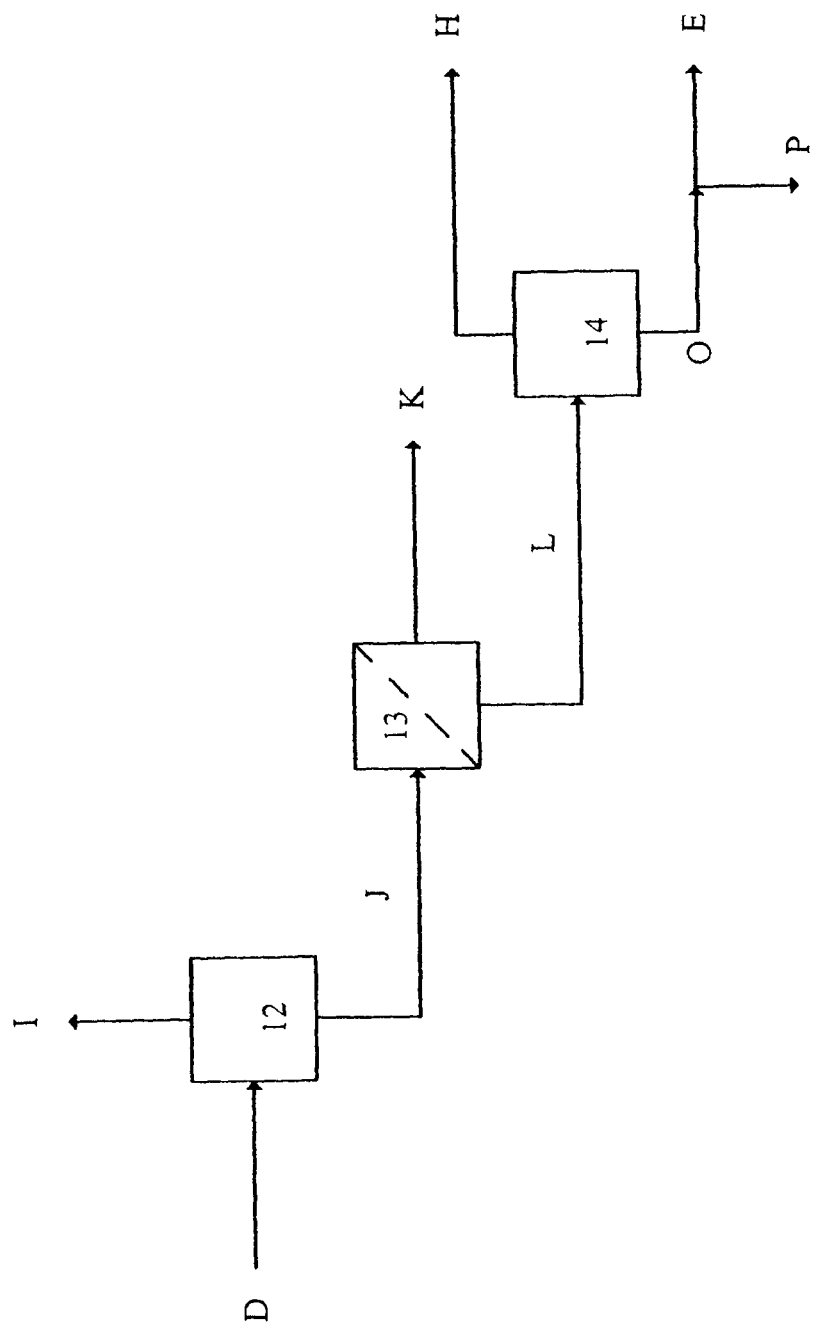
FIG. 6 shows one aspect of product recovery according to the present invention.

The separation system, illustrated in FIG. 6, comprises a gas-liquid separator 12, separating the gas products in stream I and the liquid products in stream J. In an aspect the gas product is used internally for fuelling the trimheater 6. The liquid products are further separated in a first membrane filter 13. The membrane filtration separation is pressure driven, and in many applications applying a nano- or ultrafiltration membrane. The filtration retentate in stream L includes parts of the feed water, the oil product and the dissolved inorganic compounds, e.g. salts from the feedstock and the homogenous catalyst. The oil product is separated from stream L in an oil separator (phase separator unit) 14 operating at atmospheric conditions, and forming the oil product stream H. The remaining water and dissolved inorganic compounds forms stream O. The main part of stream O is recycled to the pre-conversion 1, 2 in stream E, thereby recycling the homogenous catalyst, while a purge stream P is discharged to balance the inorganic compound input from the feedstock.

Figure 7:
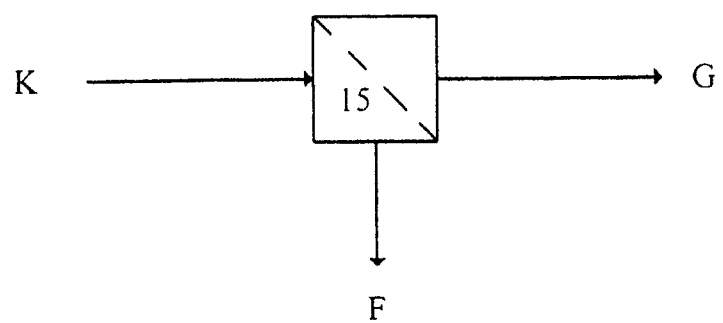
FIG. 7 shows another aspect of product recovery according to the present invention.
Figure 8:
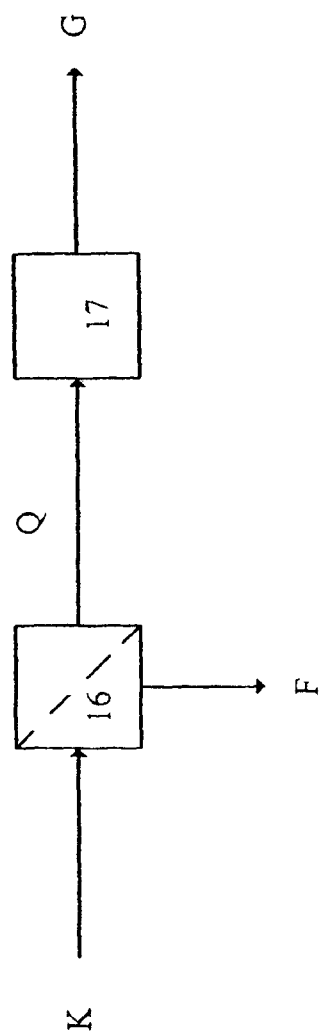
FIG. 8 shows yet another aspect of product recovery according to the present invention.
Figure 9:
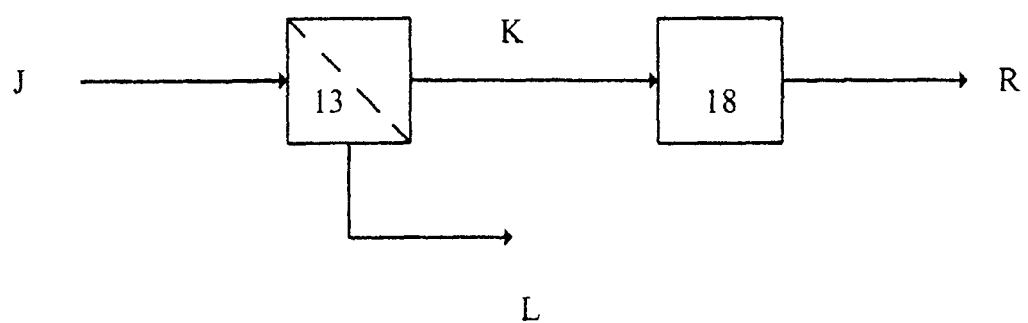
FIG. 9 shows yet another aspect of product recovery according to the present invention.

The further processing of the membrane filtration permeate, denoted stream K, is illustrated in FIG. 7-9. Stream K contains smaller water soluble organics like C 1-4 alcohols and carboxylic acids.

In one aspect illustrated in FIG. 7 stream K is fed to a separation unit (membrane filter) 15, producing pure water of drinking water quality in stream G and a stream of water soluble organics in stream F. The separation unit 15 is in an aspect of the invention a reverse osmosis membrane unit, comprising a multitude of membrane modules. The retained water soluble organics in stream F are recycled to the pre-conversion step 1, 2. In a further aspect, illustrated in FIG. 8, stream K is split into a concentrated water soluble organics stream F and an organics depleted water stream Q. The separation unit 16 involved is in many applications a membrane separation driven by temperature or concentration gradients, like membrane distillation or pervaporation.

The water stream Q is further purified in a polishing step 17, producing the pure water stream G. The polishing step 17 is preferably an activated carbon filter or like means for absorption of very low concentrations of impurities from a water stream.

In an aspect illustrated in FIG. 9 the water soluble organic stream K is fed to a direct methanol fuel cell 18, producing electricity and a process water stream R. The direct methanol fuel cell 18 might include feed stream and effluent conditioning steps.

EXAMPLES

Illustrative Example 1

Conversion of Sewage Sludge

Anaerobic digested sewage sludge below was converted according to the method of the present invention in the laboratory scale plant shown in FIG. 1.

The dry matter content of the sewage sludge was 5%. The main components of the dry matter in weight % were:
C=28.3%
H=4.33%
N=3.55%
O=28.4%
P=4.49%
Al=7.77%
Si=7.44%
Ca=6.95%
Fe=3.17%
K=1.62%

An elemental analysis of sewage sludge dry matter was further analyzed by induced coupled plasma (ICP) revealing the following composition:

| C [%] | O [%] | Al [%] | H [%] | Ca [%] | Si [%] | N [%] | P [%] | K [%] |
|---|---|---|---|---|---|---|---|---|
| 30.9 | 30.5 | 6.15 | 5.2 | 5.03 | 4.98 | 4.66 | 4.62 | 2.36 |

| Cl [%] | S [%] | Fe [%] | Na [%] | Mg [%] | Zn [%] | Ti [%] | Ba [%] | Mn [%] |
|---|---|---|---|---|---|---|---|---|
| 1.13 | 1.09 | 1.04 | 0.938 | 0.875 | 0.226 | 0.195 | 0.0652 | 0.0375 |

The combustible fraction amounts to 58% of the dry matter content, with a heat value of 22.2 MJ/kg, which translates into a calorific value of 476 KJ/kg in the sewage sludge as received.

Prior to the test the sewage sludge was pre-treated by sizing to less than 1 mm by cutting longer particles by a Seepex macerator (type 25/15-I-I-F12-2) and milling by a colloid mill (Probst und Class, type N100/E), and filtered by a screen basket filter (mesh width 1 mm).

Subsequently 1.5% by weight of potassium in the form of potassium carbonate was added to the resulting slurry. The pH value of the slurry was 9.0.

125 ml of $ZrO_2$ heterogeneous catalyst stabilized with 2.2 atomic mole % of Si. The catalyst in the form of cylindrical pellets of 3 mm length and a diameter of 3 mm was added to the tubular reactor.

63 g/h of the pre-treated sewage sludge was pressurized to 250 bars and heated to 230 C in the pre-heating step. This stream was mixed with 393 g/h of pressurized water heated to a temperature so as to obtain a substantially constant temperature of 360±5 C after mixing.

The mixed flow was subsequently contacted with the heterogeneous catalyst in the reactor. The feed to water ratio translates into a water to feed ratio of 6:1, and the total flow of 456 g/h translates into a contact time of approximately 4 minutes.

After to the contact with the heterogeneous catalyst, the fluid containing the converted organic material is cooled to ambient temperature, filtered through a particle filter for collection of suspended particles, and expanded to ambient pressure. The liquid fraction on the stream was collected in a liquid trap, and the gas is vented off.

The experiment resulted in three product streams, a gas, an aqueous product and a solid precipitate. Samples for analysis were collected for a period of 15.5 hours.

Gas Analysis

The flow rate and composition of the produced gas was measured continuously by a gas meter with sampling. The composition was measured by gas chromatography.

The analysis of the gas phase revealed the following results:

| Gas analysis | |
|---|---|
| Hydrogen [vol. %] | 55.13 |
| Carbon dioxide [vol. %] | 31.92 |
| Carbon monoxide [vol. %] | 0.00 |
| Methane [vol. %] | 12.87 |
| Ethene [vol. %] | 0.00 |
| Ethane [vol. %] | 0.00 |
| Propene [vol. %] | 0.00 |
| Propane [vol. %] | 0.00 |
| C4-compounds [vol. %] | 0.00 |
| Total [vol. %]: | 99.92 |
| Total amount of carbon, g | 0.91 |

Liquid Analysis

The liquid product was contained suspended particles. The filtered liquid was analyzed by ion chromatography, Induced Plasma Emission (ICP) and high temperature total carbon analyzers and mass spectrometry.

The analysis of the liquid phase revealed the following results:

| Liquid analysis | |
|---|---|
| pH | 8.32 |
| Total Organic Carbon (TOC), [ppm by weight] | 726.8 |
| Total Inorganic Carbon (TIC), [ppm by weight] | 361.5 |
| Total Carbon, [ppm by weight] | 1088.3 |
| Methanol [ppm by weight] | 600 |
| Ethanol [ppm by weight] | 300 |
| Acetic acid [ppm by weight] | 332.7 |
| Formic acid [ppm by weight] | 10.3 |
| Acetaldehyde [ppm by weight] | 104.9 |
| Total amount of carbon in liquid | 9.30 g |

The inorganic carbon content in the liquid was found primarily to be due to the presence of carbonate.

Solid Analysis

The solid fractions were analyzed by means of a total carbon analyzer and by elemental analysis by an induced coupled plasma analyzer (ICP). An organic phase was found to be adsorbed to the inorganic particles under the experimental conditions used.

This organic phase was extracted prior to the solid analysis using $CH_2Cl_2$. The extractable fraction of the organic carbon was found to be an oil phase, primarily consisting of saturated hydrocarbons with a chain length of 12 to 16 carbon atoms, and there for comparable to fuel or diesel oil. The oil contained 2-hexadecanone, heptadecane, 6,10-dimethyl-2-undecanone, hexadecane, 3-methyl-indole, 2-tridecanone and other compounds. A sulphur and halogen analysis performed at the extracted oil, showed that the oil was essentially free of sulphur and halogen compounds. The total amount of oil extracted from the solids was 3.86 g and the total amount of carbon found in the oil phase was equivalent to 3.28 g.

No carbon was detected in the solid product after extraction of adsorbed oil, indicating 100% conversion of the organic material in the feed. The same result can be concluded from the carbon balance below:

| Carbon balance | | |
|---|---|---|
| Input C: | Output C: | |
| Sewage sludge: 13.81 g | 0.91 g gas C⇒ | 4.97% |
| $K_2CO_3$: 4.51 g | 4.34 g TIC liquid⇒ | 23.68% |
| | 9.3 g TOC liquid⇒ | 50.74% |
| | 0.0 TOC solid⇒ | 0.00% |
| | 3.28 g C in oil⇒ | 17.9% |
| Σ 18.33 g | Σ 17.83 g conversion⇒ | 97.3% |

| Energy balance: | | | |
|---|---|---|---|
| Component | Heat Value [kJ/kg] | Amount [g] | Energy Fraction [% of energy input with feed] |
| Feed sludge | 476 | 976.5 | |
| Methane | 50,400 | 0.25 | 2.71 |
| Hydrogen | 240,103 | 0.21 | 10.8 |
| Methanol | 19,918 | 13.67 | 58.6 |
| Oil | 41,900 | 3.86 | 34.8 |
| Sum | | | 107.0 |

Illustrative Example 2

Conversion of Sewage Sludge

Anaerobic digested sewage sludge with characteristics as given above in example was preheated and converted using the same catalyst and experimental set-up.

140 g/h of the pretreated sewage sludge was pressurized to 250 bar and heated to 230 C in the pre-heating step. This stream was mixed with 414 g/h of pressurized water heated to a temperature so as to obtain a substantially constant temperature of 300±5 C after mixing.

The mixed flow was subsequently contacted with the heterogeneous catalyst in the reactor. The feed to water ratio translates into a water to feed ratio of 3:1, and the total flow of 545 g/h translates into a contact time of 3.3 minutes.

After to the contact with the heterogeneous catalyst, the fluid containing the converted organic material is cooled to ambient temperature, filtered through a particle filter for collection of suspended particles, and expanded to ambient pressure. The liquid fraction on the stream is collected in a liquid trap, and the gas is vented off.

The experiment resulted in three product streams, a gas, an aqueous product and a solid precipitate. Samples for analysis were collected for a period of 10.5 hours.

Gas Analysis

The analysis of the gas phase revealed the following results:

| Gas analysis | |
|---|---|
| Hydrogen [vol. %] | 31.36 |
| Carbon dioxide [vol. %] | 41.17 |
| Carbon monoxide [vol. %] | 2.25 |
| Methane [vol. %] | 24.22 |
| Ethene [vol. %] | 0.00 |
| Ethane [vol. %] | 0.00 |
| Propene [vol. %] | 0.00 |
| Propane [vol. %] | 0.00 |
| C4-compounds [vol. %] | 0.00 |
| Total [vol. %]: | 99.00 |
| Total amount of carbon, g | 0.54 |

Liquid Analysis

The analysis of the liquid phase revealed the following results:

| Liquid analysis | |
|---|---|
| pH | 7.42 |
| Total Organic Carbon (TOC), [ppm by weight] | 985.1 |
| Total Inorganic Carbon (TIC), [ppm by weight] | 439.3 |
| Total Carbon, [ppm by weight] | 1424.4 |
| Methanol [ppm by weight] | 800 |
| Ethanol [ppm by weight] | 0 |
| Acetic acid [ppm by weight] | 347.2 |
| Formic acid [ppm by weight] | 43.2 |
| Acetaldehyde [ppm by weight] | 156.5 |
| Total amount of carbon in liquid | 13.33 g |

The inorganic carbon content in the liquid was found primarily to be due to the presence of carbonate.

Solid Analysis

The solid fractions were analyzed by means of a total carbon analyzer. An organic phase was found to be adsorbed to the inorganic particles under the experimental conditions used.

This organic phase was extracted prior to the solid analysis using $CH_2Cl_2$. The extractable fraction of the organic carbon was found to be an oil phase, primarily consisting of saturated hydrocarbons with a chain length of 12 to 16 carbon atoms, and there for comparable to fuel or diesel oil. The oil contained 2-hexadecanone, heptadecane, 6,10-dimethyl-2-undecanone, hexadecane, 3-methyl-indole, 2-tridecanone and other compounds. The total amount of oil extracted from the solids was 12.73 g and the total amount of carbon found in the oil phase was equivalent to 10.83 g.

No carbon was detected in the solid product after extraction of adsorbed oil, indicating 100% conversion of the organic material in the feed.

| Carbon balance: | | |
|---|---|---|
| Input C: | Output C: | |
| Sewage sludge: 20.58 g | 0.54 g gas C⇒ | 1.97% |
| $K_2CO_3$: 6.78 g | 6.43 g TIC liquid⇒ | 23.5% |
| | 6.3 g TOC liquid⇒ | 23.02% |
| | 0.0 TOC solid⇒ | 0.00% |
| | 10.83 g C in oil⇒ | 39.58% |
| Σ 27.36 g | Σ 24.1 g conversion⇒ | 88.1% |

| Energy balance: | | | |
|---|---|---|---|
| Component | Heat Value [kJ/kg] | Amount [g] | Energy Fraction [% of energy input with feed] |
| Feed sludge | 476 | 1470 | |
| Methane | 50,400 | 0.28 | 2.01 |
| Hydrogen | 240,103 | 0.07 | 2.40 |
| Methanol equivalents | 19,918 | 9.30 | 26.37 |
| Oil | 41,900 | 12.73 | 76.2 |
| Sum | | | 107.0 |

Illustrative Example 3

Conversion of Corn Silage

Corn silage was pretreated and converted using the same catalyst and experimental set-up as described above in example 1 and 2.

Prior to the test the sewage sludge was pretreated by sizing to less than 1 mm by cutting longer particles by a Seepex macerator (type 25/15-I-I-F12-2) and milling by a colloid mill (Probst und Class, type N100/E), and filtered by a screen basket filter (mesh width 1 mm).

Subsequently 1.5% by weight of potassium in the form of potassium carbonate was added to the resulting slurry. The pH value of the slurry was 9.6.

The characteristics of the corn silage after the pretreatment were the following:

| Corn silage feedstock | |
|---|---|
| Dry matter content [% weight] | 11.29 |
| Inorganic fraction of dry matter [% Weight] | 29.4 |
| Density [kg/m$^3$] | 1.0099 |
| pH | 9.6 |
| Heat of combustion[1] [kJ/kg] | 1435 |

[1]Based on 18 MJ/kg heat of combustion for the organic fraction of the dry matter.

The inorganic content of the dry matter was mainly the added potassium carbonate, accounting for approximately ¾ of the dry matter inorganic compounds.

GC-MS analysis of the corn silage feedstock revealed numerous compounds, but all were present in concentrations too low for identification. Particularly aromatics like phenols were not found in any significant amount.

The dry matter content of the corn silage feedstock was analyzed, revealing the following composition:

| Corn silage dry matter | | | |
|---|---|---|---|
| TC [mg/kg] | 325000 | Mo [mg/kg] | 7.82 |
| TOC [mg/kg] | 315000 | N [mg/kg] | 6960 |
| Al [mg/kg] | 233 | Na [mg/kg] | 825 |
| Ca [mg/kg] | 2023 | Ni [mg/kg] | 11.1 |
| Cl [mg/kg] | 1682 | S [mg/kg] | <0.1 |
| Cr [mg/kg] | 28 | Si [mg/kg] | 2090 |
| Fe [mg/kg] | 4571 | Zr [mg/kg] | 2.24 |
| K [mg/kg] | 112350 | | |

140 g/h of the pretreated sewage sludge was pressurized to 250 bar and heated to 230 C in the pre-heating step. This stream was mixed with 377 g/h of pressurized water heated to a temperature so as to obtain a substantially constant temperature of 350±5 C after mixing.

The mixed flow was subsequently contacted with the heterogeneous catalyst in the reactor. The feed to water ratio translates into a water to feed ratio of 3.75:1, and the total flow of 517 g/h translates into a contact time of 3.3 minutes.

After the contact with the heterogeneous catalyst, the fluid containing the converted organic material was cooled to ambient temperature, filtered through a particle filter for collection of suspended particles, and expanded to ambient pressure. The liquid fraction on the stream is collected in a liquid trap, and the gas is vented off.

The experiment resulted in four product streams, a gas, an aqueous product, a free oil phase and a solid precipitate. Samples for analysis were collected for a period of 16 hours.

Gas Analysis

The analysis of the gas phase revealed the following results:

| Gas analysis | |
|---|---|
| Hydrogen [vol. %] | 7.5 |
| Carbon dioxide [vol. %] | 88.74 |
| Carbon monoxide [vol. %] | 0.00 |
| Methane [vol. %] | 0.33 |
| Ethene [vol. %] | 0.06 |
| Ethane [vol. %] | 0.06 |
| Propene [vol. %] | 0.25 |
| Propane [vol. %] | 0.05 |
| C4-compounds [vol. %] | 0.00 |
| Total [vol. %]: | |
| Total amount of carbon, g | 15.2 |

Liquid Analysis

The analysis of the liquid phase revealed the following results:

| Liquid analysis | |
|---|---|
| pH | 8.30 |
| Total Organic Carbon (TOC), [ppm by weight] | 2105 |
| Total Inorganic Carbon (TIC), [ppm by weight] | 201 |
| Total Carbon, [ppm by weight] | 2305 |
| Methanol [vol %] | 1.64 |
| Ethanol [vol %] | 0.27 |
| Acetic acid [ppm by weight] | 5185 |
| Formic acid [ppm by weight] | 2206 |
| Glycol acid | 10470 |
| Acetaldehyde [ppm by weight] | 115.0 |
| Total amount of carbon in liquid | 40.1 g |

The inorganic carbon content in the liquid was found primarily to be due to the presence of carbonate.

Solid Analysis

The solid fractions were analyzed by means of a total carbon analyzer. An organic phase was found to be adsorbed to the inorganic particles under the experimental conditions used.

This organic phase was extracted prior to the solid analysis using $CH_2Cl_2$. The extractable fraction of the organic carbon was found to be an oil phase, primarily consisting of saturated hydrocarbons with a chain length of 12 to 16 carbon atoms, and there for comparable to fuel or diesel oil. The oil contained phenol, toluene, 4-ethyl-phenol, 4-ethyl-3-methylphenol, cyclopent-2-ene-1-one 2,3,4 trimethyl, 2-methyl-1-penten-3-yne and other compounds. A sulphur analysis of the oil showed that the oil phase was essentially free of sulphur. A similar analysis for halogen compounds showed that the oil phase was essentially free of halogen. The total amount of oil extracted from the solids was 14.76 g and the total amount of carbon found in the oil phase was equivalent to 12.55 g.

No carbon was detected in the solid product after extraction of adsorbed oil, indicating 100% conversion of the organic material in the feed. The same result can be concluded from the carbon balance below:

Carbon balance:

| Input C: | Output C: | |
|---|---|---|
| Corn silage feed: 82.19 g | 15.2 g gas C⇒ | 18.5% |
| | 40.1 g TOC liquid⇒ | 48.8% |
| | 0.0 TOC solid⇒ | 0.0% |
| | 28.35 g C in oil⇒ | 34.5% |
| Σ 82.19 g | Σ 83.62 g conversion⇒ | 101.8% |

Energy balance:

| Component | Heat Value [kJ/kg] | Amount [g] | Energy Fraction [% of feed energy content] |
|---|---|---|---|
| Feed sludge | 476 | 2240 | |
| Hydrogen | 240,103 | 0.07 | 1.6 |
| Methanol | 19,918 | 28.9 | 17.9 |
| Ethanol | 28,200 | 4.20 | 4.2 |
| Glycol acid | 14,400 | 0.41 | 10.4 |
| Acetic acid | 18,200 | 1.23 | 6.5 |
| Oil | 41,900 | 14.76 | 45.1 |
| Sum | | | 85.7 |

Illustrative Example 4

Use of Microwave Heating in a Catalytic Liquid Conversion Process

In a preferred embodiment according to the present invention for conversion of organic material in high pressure water is given in the FIGS. 1-6.

An alternative embodiment, which may be advantageous in many applications according to the present invention, is the use of microwave heating for at least part of the heating process.

Such heating by combining existing microwave generators (known from kitchen microwave owens) combined with high pressure cells comprises a transparent window and may have one or more of the following advantages compared to conventional heaters based on electrical heat and/or superheated steam and/or other heat transfer fluids:

a. Improved heat transfer efficiency
b. Extremely short response time
c. Very accurate process control
d. Hot spots are avoided
e. High temperature heat transfer surfaces is avoided
f. Less thermal cracking of the organic content
g. Higher conversion rates
h. High temperature uniformity
i. Increased conversion capacity
j. Increased energy efficiency of the overall process
k. Reduction of temperature needed for conversion
l. Reduction the size of heat exchangers and cost of heat recovery in general
m. Reduced chemical consumption and/or allow other catalysts to be used
n. Simplification of the overall process and/or the related capital and/or operating costs
o. Smaller foot print Such microwave heating generally involve heating by magnetron systems operating within the frequency domain of microwaves and/or hyper-frequencies such as frequencies in the range from 300 MHz to 300 GHz such as in the range 500 MHz to 5 GHz. A microwave heating system may comprise multiple magnetrons, which may increase the overall microwave efficiency by reducing the thermal losses.

Different frequencies may initiate different energy transfer mechanisms within the materials being treated, which may be used to impact on reaction thermodynamics or product quality.

A further attractive effect of the microwave heating may be the opportunity to significantly reduce the temperature needed for a given conversion of organics according to the present invention. Hence, in a preferred embodiment of the present invention the maximum temperature in the process is below 300° C. such as below 275° C., and preferably below 250° C. such as below 225° C., and even more preferably below 175° C. Depending on the specific materials being converted the temperature may be as low as 150° C. such as in the range 110-150° C.

In a particularly preferred embodiment the maximum temperature is substantially the same as in said pretreatment step according o the present invention.

Additionally the following are definitions used in the description of the present invention.

The term hydrocarbon fuel is in the present invention intended to define all hydrocarbon based fuels, which may or may not comprise other elements than carbon and hydrogen, e.g. some of said hydrocarbons may comprise oxygen and other elements e.g. in the form of groups of alcohols, aldehydes, ketones, carboxylic acid, ester, esthers etc. and reaction products thereof.

The membrane processes of the present invention is well known in the prior art (e.g. W. S. HO et al, "Membrane Handbook", Van Nordstrand Reinhold, p. 103-132, p. 263-446, 1992, ISBN 0-442-23747-2, K. Scott, "Handbook of Industrial Membranes" Elsevier Science Publishers, 1995, p. 3-163, p. 331-355, p. 575-630, ISBN 1 85617 233 3)

The surface areas referred to throughout this specification and claims are, preferably, the nitrogen BET surface areas determined by the method described in the article by Brunauer, P. Emmett and E. Teller, J. Am. Chem. Soc., Vol. 60, p. 309 (1938). This method depends on the condensation of nitrogen into the pores, and is effective for measuring pores with pore diameters in the range of 10 Å to 600 Å. The volume of nitrogen adsorbed is related to the surface area per unit weight of the support.

It is well known in the prior art that the activity of a catalyst is proportional to the surface area (BET), and that catalysts may show a significant activity drop over time, when subjected to e.g. hydrothermal conditions as used in relation to the present invention. In order to minimize such potential activity loss a surface area stabilizer is incorporated into the heterogeneous catalyst.

Red Mud is a waste product of bauxite processing via the Bayer process. It comprises oxides and hydroxides of mainly aluminium, iron, titanium, silicon, and sodium.

The invention claimed is:

1. A method for converting organic material into a hydrocarbon fuel, the method comprising:
(i) conducting a fermentation process that results in the fermentation of an organic material and which fermentation process results in the production of a fermented fluid material comprising a fermentation broth which contains a hydrocarbon fuel;

(ii) conducting a separation process whereby the resultant fluid fermented material is separated into a hydrocarbon fuel and a residual product;

(iii) conducting a conversion process wherein at least part of the separated residual product is converted into energy, wherein said conversion process is effected in a high pressure fluid comprising a pressure of at least 50 bar, and further wherein said high pressure fluid is selected from water, or alcohols and combinations thereof, and still further wherein said conversion process includes a hydrothermal conversion, solvothermal conversion or both a hydrothermal and solvothermal conversion, and further wherein at least one homogeneous catalyst, or one heterogeneous catalyst or combination thereof is present in said high pressure fluid; and (iv) distributing or recirculating at least some of the energy produced by the conversion process to the fermentation process, comprising directly or indirectly converting sugar(s) contained in the fermentation broth comprising hydrocarbon fuel(s) by the use or addition of one or more microbia.

2. The method of claim 1, wherein the separation process in (ii) comprises separating out a first stream comprising oils and a second stream comprising water soluble organics.

3. The method of claim 2, wherein water soluble salts are separated out in the first stream, in the second stream, or in both the first and second stream.

4. The method of claim 1, wherein the separation process in (ii) comprises filtration.

5. The method of claim 3, wherein the separation process in (ii) comprises filtration.

6. The method according to claim 1, wherein said conversion process that converts the residual material generates thermal energy or heat.

7. The method according to claim 1, wherein the pretreatment steps comprise a liquefaction step, wherein the organic material is liquefied by the addition of enzymes.

8. The method according to claim 1, wherein the pretreatment steps include a saccharification step, wherein the organic material is saccharified by the addition of enzymes.

9. The method according to claim 1, wherein in step (iv) at least 50% of the energy required for said pre-treatment process is supplied by distributing some of the energy produced by the conversion process (iii) to the fermentation process.

10. The method according to claim 1, wherein the fermentation process of step (i) takes place in a fluid.

11. The method according to claim 10, wherein the fluid comprises water.

12. The method according to claim 1, further comprising directly or indirectly converting sugar(s) contained in the fermentation broth comprising hydrocarbon fuel(s) by the use or addition of one or more microbia.

13. The method according to claim 12, wherein said one or more microbia include yeast and bacteria.

14. The method according to claim 12, wherein said one or more microbia include thermolabile bacteria.

15. The method according to claim 1, wherein the fermentation process (i) is effected at a temperature ranging from 24-36 degrees C. for 24-96 hours at a pH of about 4-5.

16. The method according to claim 1, wherein the separation process in (ii) comprises distilling the fermentation broth thereby separating at least a part of the hydrocarbon fuel from the remainder of the fermentation broth (residual product).

17. The method according to claim 16, wherein substantially all of the hydrocarbon fuel present in the fermentation broth is separated from the remainder of the fermentation broth (residual product) by distillation.

18. The method according to claim 1, wherein at least 50% of the energy required for said separation process in step (ii) is supplied by distributing at least some of the energy generated by the conversion process in step (iii) to the fermentation process of step (i).

19. The method according to claim 1, wherein at least 50% of the energy required for said pre-treatment process, fermentation process in step (i), and separation process of step (ii) is supplied by said energy distribution process in step (iv).

20. The method according to claim 1, wherein said conversion process in step (iii) comprises a gasification and/or pyrolysis process.

21. The method according to claim 1, wherein said conversion process in step (iii) comprises a combustion process.

22. The method according to claim 1, wherein said conversion process in step (iii) is conducted in a high pressure fluid at a pressure of least 100 bar.

23. The method according to claim 1, wherein said conversion process in step (iii) is conducted in a high pressure fluid at a pressure of least 150 bar.

24. The method according to claim 1, wherein said conversion process in step (iii) is conducted in a high pressure fluid at a pressure of least 200 bar.

25. The method according to claim 1, wherein said conversion process in step (iii) is conducted in a high pressure fluid at a pressure of least 250 bar.

26. The method according to claim 1, wherein said conversion process is effected by at least one method selected among supercritical water oxidation, wet gasification, or liquefaction or a combination of any of the foregoing methods.

27. The method according to claim 1, wherein said at least one homogeneous catalyst, heterogeneous catalyst, or combination thereof used in the conversion process of step (iii) comprises at least one compound which contains at least one element from group I of the periodic table, or at least one compound which contains at least one element from group IV of the periodic table, or comprises a combination of any of the foregoing.

28. The method according to claim 1, wherein said at least one homogeneous or heterogeneous catalyst or combination thereof is contained in the ash fraction of said substances being fed to said conversion step.

29. The method according to claim 1, wherein the conversion process in step (iii) comprises the following steps:

(1) pressurizing said residual product in the fluid to a pressure above 225 bar, (2) heating said residual product in said fluid to a temperature above 200 C in the presence of a homogeneous catalyst comprising a compound which contains at least one element of group IA of the periodic table of elements, and (3) contacting said residual product in said fluid with a heterogeneous catalyst comprising a compound which contains at least one element of group IVB of the periodic table, or alpha-alumina or a combination thereof.

30. The method according to claim 29, further comprising ensuring that said fluid initially has a pH value of above 7.

31. The method according to claim 30, wherein said fluid initially is adjusted to have an initial pH value above 7 prior to the conversion process in step (iii).

32. The method according to claim 29, further comprising the step of maintaining the pH value of said fluid containing said residual product in the range 7-14.

33. The method according to claim 29, further comprising the step of maintaining the pH value of said fluid containing said residual product in the range 7-12.

34. The method according to claim 29, further comprising the step of maintaining the pH value of said fluid containing said residual product in the range 7-10.

35. The method according to claim 29, further comprising the step of maintaining the pH value of said fluid containing said residual product in the range 8-10.

36. The method according to claim 29, further comprising pre-treating the residual product at a pressure of 4-15 bar at the temperature of 100-170 degrees C. for a period of 0.5-2 hours.

37. The method according to claim 29, which further comprises separating the water and water soluble organics in the fluid fermented material from the oil and water soluble salts using a first separation unit, and further wherein the water soluble organics comprise up-concentrated methanol which is re-circulated to the organic material which is pre-treated prior to fermentation step (i).

38. The method according to claim 29, wherein the step (3) of contacting the residual product in the fluid with a heterogeneous catalyst is effected while the temperature is maintained substantially constant.

39. The method according to claim 29, wherein the temperature in the step of contacting ranges from 200-650 degrees C.

40. The method according to claim 29, wherein the temperature in the step of contacting ranges from 200-450 degrees C.

41. The method according to claim 29, wherein the temperature in the step of contacting ranges from 200-374 degrees C.

42. The method according to claim 29, wherein the temperature in the step of contacting ranges from 250-374 degrees C.

43. The method according to claim 29, wherein the temperature in the step of contacting ranges from 275-350 degrees C.

44. The method according to claim 29, wherein the pressure used to effect said conversion ranges from 225-600 bars.

45. The method according to claim 29, wherein the pressure used to effect said conversion ranges from 225-400 bars.

46. The method according to claim 29, wherein the pressure used to effect said conversion ranges from 225-350 bars.

47. The method according to claim 29, wherein the pressure used to effect said conversion ranges from 240-300 bars.

48. The method according to claim 29, wherein said heterogeneous catalyst in step (3) is in the form selected from a suspended particle, tablet, pellet, ring, cylinder, a honey comb structure, or a fibrous structure or a combination of any of the foregoing.

49. The method according to claim 29, further comprising the step of re-circulating carbonates, or hydrogen carbonates or a combination thereof.

50. The method according to claim 29, further comprising the step of re-circulating at least one alcohol.

51. The method according to claim 29, further comprising the step of re-circulating a fluid containing hydrogen.

52. The method according to claim 29, further comprising the step of re-circulating at least one carboxylic acid.

53. The method according to claim 29, further comprising the step of re-circulating at least one aldehyde, or at least one ketone, or a combination of the foregoing.

54. The method according to claim 29, wherein said fluid comprises water and the water concentration is at least 5% by weight of said fluid.

55. The method according to claim 54, wherein the water concentration is at least 10% by weight of said fluid.

56. The method according to claim 54, wherein the water concentration is at least 20% by weight of said fluid.

57. The method according to claim 54, wherein the water concentration is at least 30% by weight of said fluid.

58. The method according to claim 54, wherein the water concentration is at least 40% by weight of said fluid.

59. The method according to claim 29, wherein said residual product is selected from the group consisting of sludge, sewage sludge, liquid manure, corn silage, clarifier sludge, black liquor, residues from fermentation, residues from juice production, residues from edible oil production, residues from fruit and vegetable processing, residues from food and drink production, leachate, and seepage water or a combination thereof.

60. The method according to claim 29, wherein said residual product is selected from lignocelulotic materials which are selected from the group consisting of biomass, straw, grasses, stems, wood, bagasse, wine trash, sawdust, wood chips, and energy crops or a combination thereof.

61. The method according to claim 29, wherein said residual product is a waste material selected from house hold waste, municipal solid waste, paper waste, auto shredder waste, plastics, polymers, rubbers, scrap tires, cable wastes, CCA treated wood, halogenated organic compounds, PCB bearing transformer oils, electrolytic capacitors, halones, medical waste, risk material from meat processing, meat and bone meal, liquid streams, or process or waste water streams containing dissolved and/or suspended residual product.

62. The method according to claim 29, wherein the concentration of said residual product in said fluid is at least 5% by weight.

63. The method according to claim 29, wherein the concentration of said residual product in said fluid is at least 10% by weight.

64. The method according to claim 29, wherein the concentration of said residual product in said fluid is at least 15% by weight.

65. The method according to claim 29, wherein the concentration of said residual product in said fluid is at least 20% by weight.

66. The method according to claim 29, wherein the concentration of said residual product in said fluid is at least 30% by weight.

67. The method according to claim 29, wherein the concentration of said residual product in said fluid is at least 50% by weight.

68. A method for converting organic material into a hydrocarbon fuel, the method comprising:
- (i) conducting a fermentation process that results in the fermentation of an organic material and which fermentation process results in the production of a fermented fluid material comprising a fermentation broth which contains a hydrocarbon fuel:
- (ii) conducting a separation process whereby the resultant fluid fermented material is separated into a hydrocarbon fuel and a residual product;
- (iii) conducting a conversion process wherein at least part of the separated residual product is converted into energy, wherein said conversion process is effected in a high pressure fluid comprising a pressure of at least 50 bar, and further wherein said high pressure fluid is selected from water, or alcohols and combinations thereof, and still further wherein said conversion process includes a hydrothermal conversion, solvothermal conversion or both a hydrothermal and solvothermal conversion, and further wherein at least one homogeneous catalyst, or one heterogeneous catalyst or combination thereof is present in said high pressure fluid; and (iv) distributing or recirculating at least some of the energy produced by the conversion process to the fermentation process, wherein the process further includes a pre-treatment process comprising one or more pre-treatment steps and wherein the pretreatment steps comprise a liquefaction step, wherein the organic material is liquefied by the addition of enzymes.

69. A method for converting organic material into a hydrocarbon fuel, the method comprising:
(i) conducting a fermentation process that results in the fermentation of an organic material and which fermentation process results in the production of a fermented fluid material comprising a fermentation broth which contains a hydrocarbon fuel:
(ii) conducting a separation process whereby the resultant fluid fermented material is separated into a hydrocarbon fuel and a residual product;
(iii) conducting a conversion process wherein at least part of the separated residual product is converted into energy, wherein said conversion process is effected in a high pressure fluid comprising a pressure of at least 50 bar, and further wherein said high pressure fluid is selected from water, or alcohols and combinations thereof, and still further wherein said conversion process includes a hydrothermal conversion, solvothermal conversion or both a hydrothermal and solvothermal conversion, and further wherein at least one homogeneous catalyst, or one heterogeneous catalyst or combination thereof is present in said high pressure fluid; and
(iv) distributing or recirculating at least some of the energy produced by the conversion process to the fermentation process, wherein the process further includes a pre-treatment process comprising one or more pre-treatment steps, and wherein the pretreatment steps include a saccharification step, wherein the organic material is saccharified by the addition of enzymes.

70. The method of claim 1, wherein the hydrocarbon fuel comprises ethanol.

71. A method for converting organic material into a hydrocarbon fuel, the method comprising:
(i) conducting a fermentation process that results in the fermentation of an organic material and which fermentation process results in the production of a fermented fluid material comprising a fermentation broth which contains a hydrocarbon fuel:
(ii) conducting a separation process whereby the resultant fluid fermented material is separated into a hydrocarbon fuel and a residual product;
(iii) conducting a conversion process wherein at least part of the separated residual product is converted into energy, wherein said conversion process is effected in a high pressure fluid comprising a pressure of at least 50 bar, and further wherein said high pressure fluid is selected from water, or alcohols and combinations thereof, and still further wherein said conversion process includes a hydrothermal conversion, solvothermal conversion or both a hydrothermal and solvothermal conversion, and further wherein at least one homogeneous catalyst, or one heterogeneous catalyst or combination thereof is present in said high pressure fluid; and
(iv) distributing or recirculating at least some of the energy produced by the conversion process to the fermentation process, wherein the fermentation process (i) is effected at a temperature ranging from 24-36 degrees C. for 24-96 hours at a pH of about 4-5.

* * * * *